US011638675B2

(12) United States Patent
Binversie et al.

(10) Patent No.: US 11,638,675 B2
(45) Date of Patent: May 2, 2023

(54) SYSTEM AND METHOD FOR HEAT OR COLD THERAPY AND COMPRESSION THERAPY

(71) Applicant: ZENITH TECHNICAL INNOVATIONS, LLC, Gurnee, IL (US)

(72) Inventors: Gregory Binversie, Readstown, WI (US); Eric Zeman, Burlington, WI (US); Joshua Hauck, Libertyville, IL (US)

(73) Assignee: Zenith Technical Innovations, LLC, Gurnee, IL (US)

(*) Notice: Subject to any disclaimer, the term of this patent is extended or adjusted under 35 U.S.C. 154(b) by 141 days.

(21) Appl. No.: 16/183,398

(22) Filed: Nov. 7, 2018

(65) Prior Publication Data
US 2020/0138665 A1    May 7, 2020

(51) Int. Cl.
*A61H 9/00* (2006.01)

(52) U.S. Cl.
CPC ... *A61H 9/0078* (2013.01); *A61H 2201/0207* (2013.01); *A61H 2201/0214* (2013.01);
(Continued)

(58) Field of Classification Search
CPC .......... A61H 9/0078; A61H 2201/0221; A61H 2201/0207; A61H 2201/0214; A61H 2201/1238; A61H 2201/5071; A61H 2201/165; A61H 2201/5046; A61H 2201/1642; A61H 2201/0242; A61H 2201/02; A61H 2201/0228; A61H 2201/0235; A61H 2201/025; A61H 2201/0257; A61H 2201/0264; A61H 1/00
(Continued)

(56) References Cited

U.S. PATENT DOCUMENTS 1,958,899 A    5/1934   MacAdams
2,146,622 A    2/1939   Carlo
(Continued)

FOREIGN PATENT DOCUMENTS

DE    3343664    2/1983
EP    0338283    10/1989
(Continued)

OTHER PUBLICATIONS

International Search Report and Written Opinion dated Dec. 31, 2019 from corresponding international application serial No. PCT/US2019/056201.
(Continued)

*Primary Examiner* — Justine R Yu
*Assistant Examiner* — Kelsey E Baller
(74) *Attorney, Agent, or Firm* — Ryan Kromholz & Manion, S.C.

(57) ABSTRACT

A medical device providing a combination of thermal and DVT therapies to a patient. The components, arrangement of components, function of the device as a whole, and methods of use of the device are all devised to maximize therapeutic effectiveness. Effectiveness in this context is measured by the ability to provide a controlled application of the recommended thermal treatment including time, temperature, compression, and number of cycles with specified cycle duration.

18 Claims, 31 Drawing Sheets

(52) U.S. Cl.
CPC .............. *A61H 2201/0221* (2013.01); *A61H 2201/0242* (2013.01); *A61H 2201/1238* (2013.01); *A61H 2201/165* (2013.01); *A61H 2201/1642* (2013.01); *A61H 2201/5046* (2013.01); *A61H 2201/5071* (2013.01)

(58) Field of Classification Search
USPC ...................................... 607/96–114; 601/15
See application file for complete search history.

(56) References Cited

U.S. PATENT DOCUMENTS

| | | |
|---|---|---|
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 2,781,041 A | 12/1957 | Weinberg |
| 2,954,898 A | 10/1960 | Freeberg |
| 3,261,042 A | 7/1966 | Baker |
| 3,320,682 A | 5/1967 | Sliman |
| 3,354,898 A | 11/1967 | Barnes |
| 3,444,922 A * | 5/1969 | Dingman .............. A61H 35/00 219/217 |
| 3,561,435 A | 2/1971 | Nicholson |
| 3,738,367 A | 6/1973 | Hardy |
| 3,744,555 A | 7/1973 | Fletcher et al. |
| 3,830,676 A | 8/1974 | Elkins |
| 3,871,381 A | 3/1975 | Roslonski |
| 3,892,229 A | 7/1975 | Taylor et al. |
| 3,901,225 A | 8/1975 | Sconce |
| 3,993,053 A | 11/1976 | Grossan |
| 4,020,209 A | 4/1977 | Yuan |
| 4,026,299 A | 5/1977 | Sauder |
| 4,030,488 A | 6/1977 | Hasty |
| 4,116,476 A | 9/1978 | Porter et al. |
| 4,147,921 A | 4/1979 | Walter et al. |
| 4,149,529 A * | 4/1979 | Copeland ............. A61H 9/0078 601/151 |
| 4,149,541 A | 4/1979 | Gammons et al. |
| 4,170,998 A | 10/1979 | Sauder |
| 4,194,247 A | 3/1980 | Melander |
| 4,311,135 A | 1/1982 | Brueckner et al. |
| 4,335,726 A | 6/1982 | Kolstedt |
| 4,338,944 A * | 7/1982 | Arkans ................... F25B 21/04 607/104 |
| 4,412,648 A | 11/1983 | Ford et al. |
| 4,436,125 A | 3/1984 | Blenkush |
| 4,460,085 A | 7/1984 | Jantzen |
| 4,471,759 A | 9/1984 | Anderson et al. |
| 4,478,436 A | 10/1984 | Hashimoto |
| 4,547,906 A | 10/1985 | Nishida et al. |
| 4,550,828 A | 11/1985 | Baldwin et al. |
| 4,597,384 A | 7/1986 | Whitney |
| 4,640,284 A | 2/1987 | Ruderian |
| 4,678,027 A | 7/1987 | Shirey et al. |
| 4,691,762 A | 9/1987 | Elkins et al. |
| 4,699,613 A | 10/1987 | Donawick et al. |
| 4,718,429 A | 1/1988 | Smidt |
| 4,738,119 A | 4/1988 | Zafred |
| 4,753,268 A | 6/1988 | Palau |
| 4,765,338 A | 8/1988 | Turner et al. |
| 4,829,771 A | 5/1989 | Koslow et al. |
| 4,844,072 A | 7/1989 | French et al. |
| 4,844,304 A | 7/1989 | Lenderink |
| 4,925,603 A | 5/1990 | Nambu |
| 4,966,435 A | 9/1990 | Shuster et al. |
| 4,964,282 A | 10/1990 | Wagner |
| 4,964,402 A | 10/1990 | Grim et al. |
| 4,976,262 A | 12/1990 | Palmacci |
| 5,002,270 A | 3/1991 | Shine |
| 5,014,695 A | 5/1991 | Benak et al. |
| 5,022,109 A | 6/1991 | Pekar |
| 5,033,136 A | 7/1991 | Elkins |
| 5,052,377 A | 10/1991 | Frajdenrajch |
| 5,052,725 A | 10/1991 | Meyer et al. |
| 5,056,563 A | 10/1991 | Glossop |
| 5,072,875 A | 12/1991 | Zacoi |
| 5,074,285 A | 12/1991 | Wright |
| 5,076,068 A | 12/1991 | Mikhail |
| 5,080,089 A | 1/1992 | Mason et al. |
| 5,080,166 A | 1/1992 | Haugeneder |
| 5,086,771 A | 2/1992 | Molloy |
| 5,097,829 A | 3/1992 | Quisenberry |
| 5,104,158 A | 4/1992 | Meyer et al. |
| 5,105,382 A | 4/1992 | Ogasawara |
| 5,113,877 A | 5/1992 | Johnson, Jr. et al. |
| 5,163,425 A | 11/1992 | Nambu et al. |
| 5,163,823 A | 11/1992 | Kinoshita et al. |
| 5,172,689 A | 12/1992 | Wright |
| 5,201,552 A | 4/1993 | Hohmann et al. |
| 5,230,335 A | 7/1993 | Johnson, Jr. et al. |
| 5,241,951 A | 9/1993 | Mason et al. |
| 5,243,706 A | 9/1993 | Frim et al. |
| 5,245,990 A | 9/1993 | Bertinin |
| 5,269,369 A | 12/1993 | Faghri |
| 5,294,156 A | 3/1994 | Kumazaki et al. |
| 5,305,712 A | 4/1994 | Goldstein |
| 5,314,455 A | 5/1994 | Johnson, Jr. et al. |
| 5,316,547 A | 5/1994 | Gildersleeve |
| 5,353,605 A | 10/1994 | Naaman |
| 5,354,101 A | 10/1994 | Anderson, Jr. |
| 5,354,103 A | 10/1994 | Torrence et al. |
| 5,383,689 A | 1/1995 | Wolfe, Sr. |
| 5,383,842 A | 1/1995 | Bertini |
| 5,395,399 A | 3/1995 | Rosenwald |
| 5,407,421 A | 4/1995 | Goldsmith |
| 5,411,533 A | 5/1995 | Dubreuil et al. |
| 5,411,541 A | 5/1995 | Bell et al. |
| 5,415,625 A | 5/1995 | Cassford et al. |
| 5,417,720 A | 5/1995 | Mason |
| 5,427,577 A | 6/1995 | Picchietti et al. |
| 5,451,201 A | 9/1995 | Prengier |
| 5,456,701 A * | 10/1995 | Stout ........................ A61F 7/02 165/46 |
| 5,466,250 A | 11/1995 | Johnson, Jr. et al. |
| 5,470,353 A | 11/1995 | Jensen |
| 5,476,489 A | 12/1995 | Koewler |
| 5,484,448 A | 1/1996 | Steele et al. |
| 5,494,074 A | 2/1996 | Ramacier, Jr. et al. |
| 5,496,358 A | 3/1996 | Rosenwald |
| 5,499,379 A | 3/1996 | Tanaka et al. |
| 5,520,622 A | 5/1996 | Bastyr et al. |
| 5,524,293 A | 6/1996 | Kung |
| 5,527,268 A | 6/1996 | Gildersleeve et al. |
| 5,533,354 A | 7/1996 | Pirkle |
| 5,539,934 A | 7/1996 | Ponder |
| 5,553,712 A | 9/1996 | Tisbo et al. |
| 5,554,119 A | 9/1996 | Harrison et al. |
| 5,556,138 A | 9/1996 | Nakajima et al. |
| 5,564,124 A | 10/1996 | Elsherif et al. |
| 5,584,798 A | 12/1996 | Fox |
| 5,630,328 A | 5/1997 | Hise et al. |
| 5,638,707 A | 6/1997 | Gould |
| 5,645,671 A | 7/1997 | Tillinghast |
| D382,113 S | 8/1997 | DuRapau |
| 5,662,239 A | 9/1997 | Heuvelman |
| 5,662,695 A | 9/1997 | Mason et al. |
| 5,672,148 A * | 9/1997 | Maunier .............. A61H 9/0078 601/148 |
| 5,674,262 A | 10/1997 | Tumey |
| 5,683,118 A | 11/1997 | Slocum |
| 5,711,155 A * | 1/1998 | DeVilbiss ............ A61F 7/0085 62/3.3 |
| 5,732,464 A | 3/1998 | Lamont |
| 5,792,216 A | 8/1998 | Kappel |
| 5,800,490 A * | 9/1998 | Patz ........................ A61F 7/007 607/108 |
| 5,833,638 A | 11/1998 | Nelson |
| 5,843,007 A * | 12/1998 | McEwen .............. A61H 9/0078 601/152 |
| 5,862,675 A | 1/1999 | Scaringe et al. |

(56) References Cited

U.S. PATENT DOCUMENTS

| | | |
|---|---|---|
| 5,865,841 A | 2/1999 | Kolen et al. |
| 5,866,219 A | 2/1999 | McClure et al. |
| 5,868,690 A | 2/1999 | Eischen, Sr. |
| 5,871,526 A * | 2/1999 | Gibbs ................ A61F 7/02 165/46 |
| 5,895,418 A | 4/1999 | Saringer |
| 5,913,885 A | 6/1999 | Klatz et al. |
| 5,920,934 A | 7/1999 | Hannagan et al. |
| 5,951,598 A | 9/1999 | Bishay et al. |
| 5,967,225 A | 10/1999 | Jenkins |
| 5,968,072 A | 10/1999 | Hite et al. |
| 5,970,519 A | 10/1999 | Weber |
| 5,980,561 A | 11/1999 | Kolen et al. |
| 5,984,885 A | 11/1999 | Gaylord, Jr. et al. |
| 5,989,285 A | 11/1999 | DeVilbiss et al. |
| 5,992,459 A | 11/1999 | Sugita et al. |
| 6,023,932 A | 2/2000 | Johnston |
| 6,030,412 A | 2/2000 | Klatz et al. |
| 6,036,107 A | 3/2000 | Aspen et al. |
| 6,036,112 A | 3/2000 | Hunsicker |
| 6,036,718 A | 3/2000 | Ledford et al. |
| 6,053,169 A | 4/2000 | Hunt |
| 6,055,670 A | 5/2000 | Parker |
| 6,074,413 A | 6/2000 | Davis et al. |
| 6,083,256 A | 7/2000 | Der Ovanesian |
| 6,109,338 A | 8/2000 | Butzer |
| 6,117,164 A | 9/2000 | Gildersleeve et al. |
| 6,125,636 A | 10/2000 | Taylor et al. |
| 6,156,059 A | 12/2000 | Olofsson |
| 6,178,562 B1 | 1/2001 | Elkins |
| 6,246,413 B1 | 6/2001 | Teo |
| 6,261,314 B1 | 7/2001 | Rich |
| 6,273,866 B2 | 8/2001 | Thomas et al. |
| 6,290,662 B1 | 9/2001 | Morris et al. |
| 6,328,276 B1 | 12/2001 | Falch et al. |
| 6,345,507 B1 | 2/2002 | Gillen |
| 6,352,550 B1 | 3/2002 | Gildersleeve et al. |
| 6,354,635 B1 | 3/2002 | Dyson et al. |
| 6,375,674 B1 | 4/2002 | Carson |
| 6,502,405 B1 | 1/2003 | Van Winkle |
| D473,315 S | 4/2003 | Miros et al. |
| D473,656 S | 4/2003 | Miros et al. |
| D473,948 S | 4/2003 | Elkins et al. |
| D476,996 S | 7/2003 | Amit et al. |
| D477,413 S | 7/2003 | Schirrmacher |
| D478,708 S | 8/2003 | Miros et al. |
| 6,679,908 B2 | 1/2004 | Shimizu |
| 6,695,872 B2 | 2/2004 | Elkins |
| 6,855,158 B2 | 2/2005 | Stolpmann |
| 6,871,878 B2 | 3/2005 | Miros |
| D504,727 S | 5/2005 | Schirrmacher et al. |
| 7,044,924 B1 | 5/2006 | Roth |
| 7,107,629 B2 | 9/2006 | Miros et al. |
| 7,198,093 B1 | 4/2007 | Elkins |
| 7,243,509 B2 | 7/2007 | Trinh et al. |
| D559,393 S | 1/2008 | Schirrmacher |
| D566,908 S | 4/2008 | Schirrmacher et al. |
| D572,044 S | 7/2008 | Miros |
| D574,019 S | 7/2008 | Amit et al. |
| 7,731,244 B2 | 6/2010 | Miros et al. |
| 7,837,638 B2 | 11/2010 | Miros et al. |
| 7,896,910 B2 | 3/2011 | Schirrmacher et al. |
| D643,579 S | 8/2011 | Hall et al. |
| D644,260 S | 8/2011 | Yang |
| 8,182,437 B2 | 5/2012 | Gasbarro et al. |
| D662,212 S | 6/2012 | Quisenberry |
| D662,213 S | 6/2012 | Quisenberry |
| D662,214 S | 6/2012 | Quisenberry |
| D679,023 S | 3/2013 | Quisenberry |
| 8,397,518 B1 * | 3/2013 | Vistakula ................ A61F 7/007 62/3.5 |
| D683,042 S | 5/2013 | Quisenberry |
| 8,485,995 B1 | 7/2013 | Maxon-Maldonado |
| 8,597,217 B2 | 12/2013 | Lowe et al. |
| 8,715,330 B2 | 5/2014 | Lowe et al. |
| 8,753,383 B2 | 6/2014 | Parish et al. |
| 8,778,005 B2 | 7/2014 | Parish et al. |
| 8,801,643 B2 | 8/2014 | Deshpande et al. |
| 8,827,935 B2 | 9/2014 | Maxon-Maldonado |
| 8,845,995 B2 | 9/2014 | Kauppinen et al. |
| 9,113,577 B2 | 8/2015 | Quisenberry |
| 9,114,053 B2 | 8/2015 | Wright et al. |
| 9,114,055 B2 | 8/2015 | Edelman et al. |
| 9,119,705 B2 | 9/2015 | Bitman et al. |
| 9,180,041 B2 | 11/2015 | Parish et al. |
| 9,192,539 B2 | 11/2015 | Parish et al. |
| 9,220,655 B2 | 12/2015 | Blondo et al. |
| 9,283,109 B2 | 3/2016 | Guyuron et al. |
| 9,295,605 B2 | 3/2016 | Yurko et al. |
| 9,421,142 B2 | 8/2016 | Malhi et al. |
| 9,433,525 B2 | 9/2016 | Parish et al. |
| 9,435,553 B2 | 9/2016 | Quisenberry |
| 9,615,967 B2 | 4/2017 | Lowe et al. |
| 9,669,233 B2 | 6/2017 | Quisenberry et al. |
| 9,719,703 B2 | 8/2017 | Quisenberry et al. |
| 9,877,409 B2 | 1/2018 | Quisenberry |
| 9,877,864 B2 | 1/2018 | Parish et al. |
| 9,907,692 B2 | 3/2018 | Binversie et al. |
| 9,943,437 B2 | 4/2018 | Lowe et al. |
| 9,950,148 B2 | 4/2018 | Quisenberry |
| 9,980,844 B2 | 5/2018 | Miros et al. |
| 10,016,583 B2 | 7/2018 | Quisenberry |
| 10,149,927 B2 | 12/2018 | Quisenberry |
| 10,350,108 B1 * | 7/2019 | Rittman, III ............ A61F 7/02 |
| 10,215,454 B2 | 9/2019 | Quisenberry |
| 2001/0018604 A1 | 8/2001 | Elkins |
| 2001/0034545 A1 | 10/2001 | Elkins |
| 2001/0034546 A1 | 10/2001 | Elkins |
| 2001/0039439 A1 | 11/2001 | Elkins et al. |
| 2001/0041621 A1 | 11/2001 | Sugiyama et al. |
| 2002/0019657 A1 | 2/2002 | Elkins |
| 2002/0082668 A1 | 6/2002 | Ingman |
| 2002/0093189 A1 | 7/2002 | Krupa |
| 2002/0108279 A1 | 8/2002 | Hubbard, II et al. |
| 2002/0138033 A1 | 9/2002 | Elkins |
| 2004/0068309 A1 | 4/2004 | Edelman |
| 2004/0068991 A1 * | 4/2004 | Banney ................ F28F 3/02 62/3.7 |
| 2004/0167594 A1 | 8/2004 | Elkins |
| 2004/0225341 A1 | 11/2004 | Schock et al. |
| 2004/0249427 A1 * | 12/2004 | Nabilsi ................ A61F 7/0085 607/104 |
| 2005/0126578 A1 * | 6/2005 | Garrison ............ A61M 16/024 128/874 |
| 2005/0131504 A1 | 6/2005 | Kim |
| 2005/0136213 A1 | 6/2005 | Seth et al. |
| 2005/0143796 A1 | 6/2005 | Augustine et al. |
| 2005/0143797 A1 | 6/2005 | Parish et al. |
| 2006/0190062 A1 | 8/2006 | Worthen |
| 2006/0200057 A1 | 9/2006 | Sterling |
| 2007/0118194 A1 | 5/2007 | Mason et al. |
| 2007/0161923 A1 | 7/2007 | Mitra |
| 2007/0161932 A1 | 7/2007 | Pick et al. |
| 2007/0203552 A1 | 8/2007 | Machold et al. |
| 2007/0282230 A1 | 12/2007 | Valderrabano et al. |
| 2008/0000474 A1 | 1/2008 | Jochle et al. |
| 2008/0058911 A1 * | 3/2008 | Parish ................ A61F 7/0085 607/104 |
| 2008/0065172 A1 | 3/2008 | Magdych |
| 2008/0067095 A1 | 3/2008 | Mueller |
| 2008/0188915 A1 | 8/2008 | Mills et al. |
| 2008/0234788 A1 | 9/2008 | Wasowski |
| 2008/0275534 A1 | 11/2008 | Noel |
| 2008/0283426 A1 | 11/2008 | Primer et al. |
| 2009/0005841 A1 | 1/2009 | Schirrmacher et al. |
| 2009/0069731 A1 | 3/2009 | Parish et al. |
| 2009/0183410 A1 | 7/2009 | Tursso et al. |
| 2010/0084125 A1 | 4/2010 | Goldstein et al. |
| 2010/0089896 A1 | 4/2010 | Bart |
| 2010/0137764 A1 | 6/2010 | Eddy |
| 2010/0139294 A1 | 6/2010 | Lowe et al. |
| 2010/0145421 A1 | 6/2010 | Tomlinson et al. |
| 2010/0161013 A1 | 6/2010 | Heaton |
| 2010/0210982 A1 | 8/2010 | Balachandran et al. |

(56) References Cited

U.S. PATENT DOCUMENTS

| | | |
|---|---|---|
| 2011/0009785 A1 | 1/2011 | Meyer et al. |
| 2011/0077723 A1 | 3/2011 | Parish et al. |
| 2011/0087142 A1 | 4/2011 | Ravikumar et al. |
| 2011/0152983 A1 | 6/2011 | Schirrmacher et al. |
| 2011/0307038 A1 | 12/2011 | Stiehr et al. |
| 2012/0227432 A1* | 9/2012 | Creech ............... A41D 13/0053 62/259.3 |
| 2013/0006154 A1 | 1/2013 | Lowe |
| 2013/0006335 A1 | 1/2013 | Lowe |
| 2013/0012847 A1 | 1/2013 | Lowe et al. |
| 2013/0079687 A1 | 3/2013 | Horst et al. |
| 2013/0238043 A1 | 9/2013 | Beardall et al. |
| 2013/0245508 A1 | 9/2013 | Maxon-Maldonado |
| 2013/0245519 A1 | 9/2013 | Edelman et al. |
| 2013/0253383 A1 | 9/2013 | Maxon-Maldonado |
| 2014/0228717 A1 | 8/2014 | Parish et al. |
| 2014/0249455 A1 | 9/2014 | Parish et al. |
| 2015/0182375 A1 | 7/2015 | Binversie et al. |
| 2015/0233647 A1 | 8/2015 | Quisenberry |
| 2015/0318588 A1 | 11/2015 | Quisenberry |
| 2015/0328042 A1 | 11/2015 | Parish et al. |
| 2015/0366703 A1* | 12/2015 | Du ......................... A61F 7/007 607/104 |
| 2016/0030236 A1 | 2/2016 | Parish et al. |
| 2016/0074210 A1* | 3/2016 | Chen ..................... A61F 7/007 607/96 |
| 2016/0262971 A1 | 9/2016 | Doron et al. |
| 2016/0338873 A1 | 11/2016 | Parish et al. |
| 2017/0181895 A1 | 6/2017 | Quisenberry |
| 2017/0189262 A1 | 7/2017 | Kane et al. |
| 2018/0050182 A1 | 2/2018 | Quisenberry |
| 2018/0055721 A1 | 3/2018 | Quisenberry |
| 2018/0235213 A1 | 8/2018 | Quisenberry |
| 2019/0015289 A1* | 1/2019 | Grimoldby ............... A61F 5/34 |
| 2019/0099287 A1* | 4/2019 | Vergara ................... A61F 7/007 |
| 2020/0016958 A1* | 1/2020 | Stasky ............... B60H 1/00271 |

FOREIGN PATENT DOCUMENTS

| | | |
|---|---|---|
| EP | 0412708 | 2/1991 |
| EP | 0535830 | 4/1993 |
| EP | 1329676 | 7/2003 |
| EP | 1393751 | 3/2004 |
| EP | 1972312 | 9/2008 |
| FR | 819022 | 10/1937 |
| GB | 2382988 | 6/2003 |
| GB | 2533850 | 7/2016 |
| GB | 2533851 | 7/2016 |
| IT | 330552 | 5/1935 |
| JP | 2000-288007 | 10/2000 |
| KR | 200153967 | 5/1999 |
| KR | 1020050040880 | 5/2005 |
| WO | WO1992/013506 | 8/1992 |
| WO | WO1992/015263 | 9/1992 |
| WO | WO1994/009732 | 5/1994 |
| WO | WO1996/026693 | 9/1996 |
| WO | WO1998/007397 | 2/1998 |
| WO | WO1999/044552 | 9/1999 |
| WO | WO2000/023016 | 4/2000 |
| WO | WO2000/055542 | 9/2000 |
| WO | WO2000/067685 | 11/2000 |
| WO | WO2011/070567 | 6/2011 |
| WO | WO2015/068163 | 5/2015 |
| WO | WO2016/014748 | 1/2016 |

OTHER PUBLICATIONS

Supplemental Search Report from EP Application No. 198817694.4 dated Jul. 15, 2022; 9 pages.

* cited by examiner

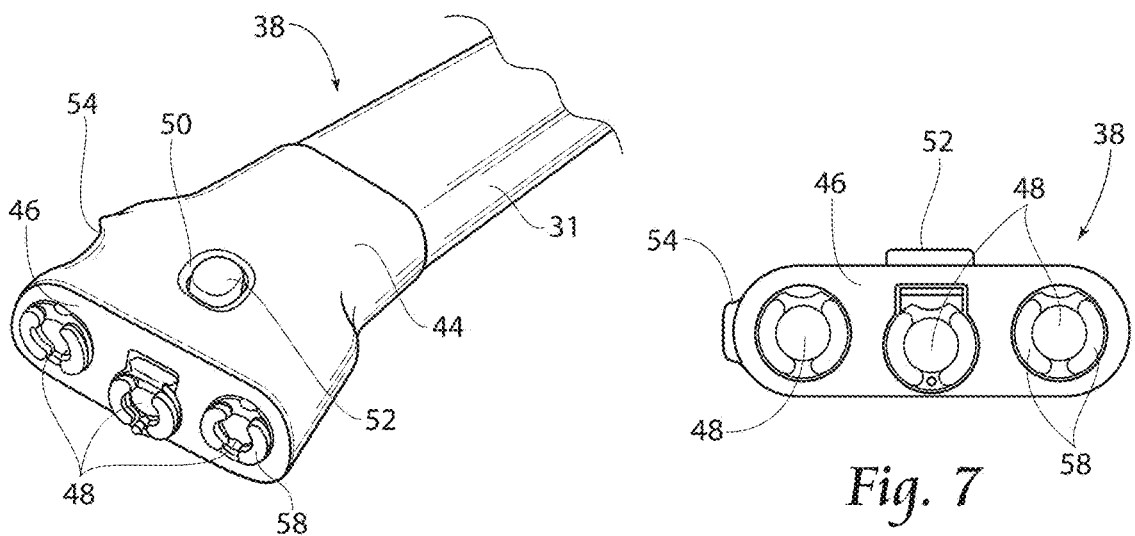
Fig. 6
Fig. 7
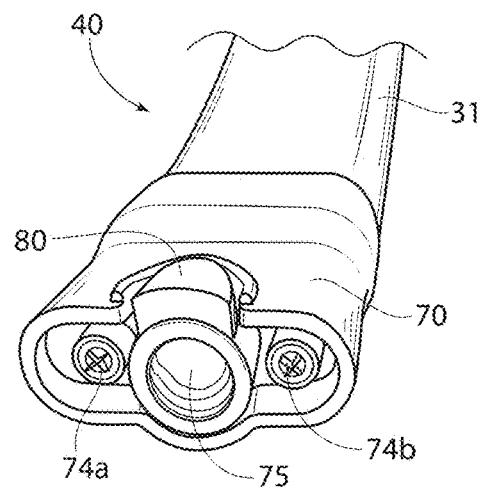
Fig. 8
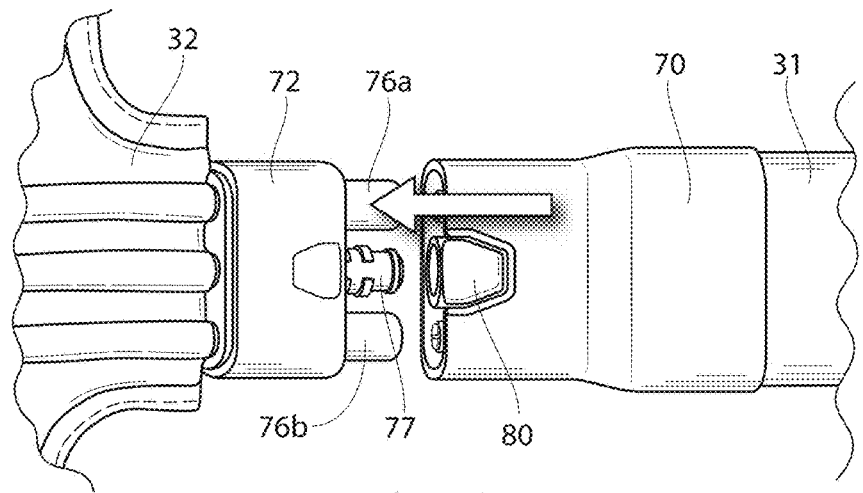
Fig. 9

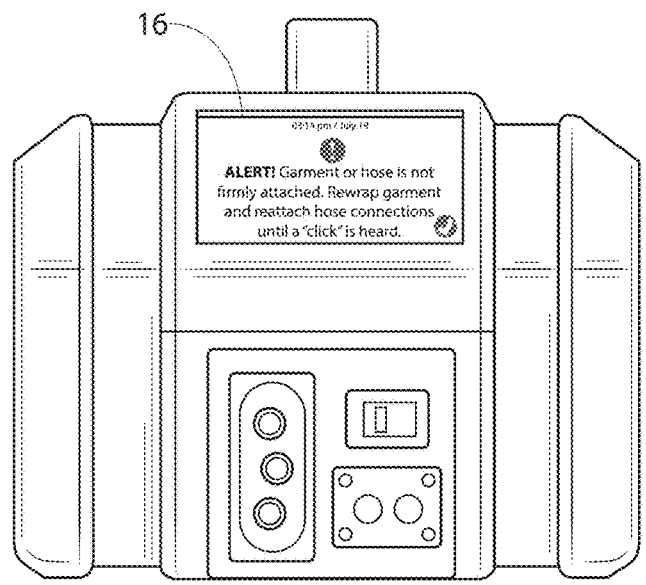
*Fig. 11*
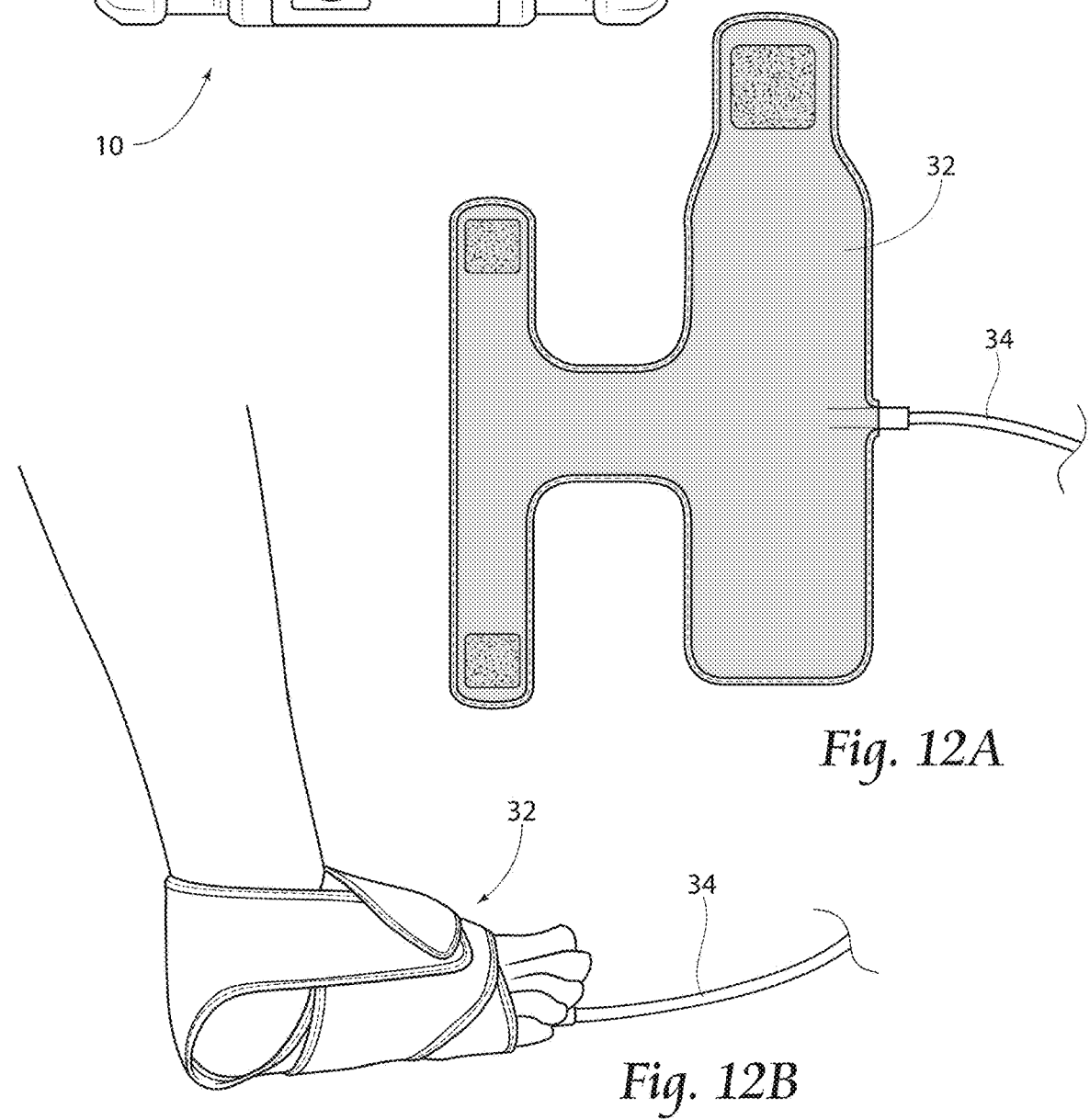
*Fig. 12A*
*Fig. 12B*

SYSTEM AND METHOD FOR HEAT OR COLD THERAPY AND COMPRESSION THERAPY

BACKGROUND OF THE INVENTION

The present invention is directed towards apparatus and methods for the treatment of medical conditions where heat or cold therapy is recommended to reduce pain and swelling. Such conditions include acute sports injuries like severe strains, sprains, contusions, and concussions, and post-surgical situations.

Outpatient treatment for such conditions typically includes instructing the patient on a therapeutic regimen to be followed at home. The apparatus and method of the present invention provides a portable heat/cold therapy unit for that purpose, among others.

There are many devices on the market for managing thermal treatment of injuries. These include electric blankets, pads, and body part shaped garments, chemical and inert products bagged for the freezer and microwave, and traditional hot water bottles and ice bags.

Perhaps the most commonly used modality is application of ice bags. These are very inexpensive and subject to shifting, dripping, and losing coldness during use. Ice bags thus need to be re-frozen and re-placed frequently in order to maintain peak thermal advantage. Ice bag therapy, to be at its most effective, must therefore be heavily supervised.

There are commercial products that require less supervision, including products having cooled water circulating through body part wraps, such as a foot wrap or elbow wrap. These can be an improvement but still do not maintain a peak thermal regimen.

Meanwhile, more robust products that are able to provide features such as temperature control, length of treatment timers, or other thermal add-ons, have not previously been portable and have been too expensive to be sent home with a patient even if possible.

There are also sophisticated and more costly devices such as those used by hospitals and surgical care physicians. However, devices that are large, expensive, and/or complex are not desirable for the therapy conditions contemplated herein.

Peltier devices, known as thermoelectric modules (TEMs), have also been on the market for a number of years. These devices have been aimed at replacing the refrigerant and heating element technology but have primarily been applied to industrial cooling applications and small coolers. TEMs in the medical device industry have been for creating cooling or heating fluids for circulation through a fitted "garment", pad or blanket for thermal treatment of injuries or post-surgery.

TEM technology eliminated the need for refrigeration and heating elements but still required a fluid reservoir and pumping system. These units have temperature sensors to control the temperature but, with a large mass of fluid to control, the unit can have significant temperature fluctuation. The temperature is controlled by turning the current on and off as well as alternating the polarity of the current to the TEM based on the temperature sensor's reading. Due to the volume of fluid needed to reach the desired temperature and the potential for heat exchange (loss or gain) through the insulated garment, it takes significant time for the fluid in the reservoir to reach and maintain the temperature.

One of the critical issues related to thermal treatment is ensuring that treatment is carried out as prescribed by the professional recommending treatment. For injuries such as strains, sprains, and minor tears, many trainers and other professionals recommend cycling 15 to 30 minutes of ice treatment followed by 30 to 45 minutes off of ice treatment continuously during waking hours for the first 24 to 72 hours after injury, depending on the severity of the injury and the patient's individual recovery rate. Very few patients maintain consistency in the process because of the continuous changes required but also because such therapy is not practical with ice-based technology.

Thermal treatments have also been used for deep vein thrombosis (DVT) treatment. DVT treatment is done with a garment compressing around leg or appendage, with the treatment usually comprised of a series off cycling between "on" (compressed) and "off" (release of pressure) states. In the "on" statement it has also been known to use a pulse a the on position, where the delivery of pressure is varied. As has been discussed in the prior art, many patients prefer such systems. See Morris, R. J. & Woodcock, J. P, (2004). Evidence-Based Compression. *Annals of Surgery*, 239(2), 162-171. Research and user feedback has indicated that the pulsed DVT prophylaxis leads to temporary relief of chronic localized pain. This is possibly related to a phenomenon known as "gate control theory" which posits that that painful stimuli can be mitigated by the activation of fβ fibers. Afβ fiber activation promotes inhibitory interneurons, which in turn inhibit the propagation of the pain signals. See Melzack, R., & Wall, P. D. (1965). Pain Mechanisms: A New Theory. *Science*, 150(3699), 971-978. When Afβ fibers are activated by "innocuous, tactile sensation", such as is provided by a pulsing DVT treatment, the perception of pain may be mitigated. See Matsumoto, M., Xie, W., Ma, L., & Ueda, H. (2008). Pharmacological switch in Aβ-stimulation-induced spinal transmission in mice with partial sciatic nerve injury. *Molecular Pain*, 4(1), 25. While such DVT treatment has been known, devices for delivery of such treatment can be improved.

Improved systems are needed chat overcome the disadvantages of prior technologies.

SUMMARY OF THE INVENTION

The medical device of the present invention can be used to provide both analgesic and thermal treatment for use with acute injuries, post-surgical use, and medical conditions where cryotherapy or heat therapy, or a cycling of each, are recommended. The device provides timed controlled temperature and compression along with optional treatments of DVT prophylaxis.

In some embodiments, the temperature, time, pressure, and DVT prophylaxis is managed by an onboard microprocessor in an attached controller using a touch screen or other input devices.

One key object of the present invention is to provide a controlled application of professionally recommended thermal treatment including time, temperature, compression, and number of cycles with specified cycle duration. This is achieved by controlled tracking of actual usage compared to recommended treatment. In some embodiments, the device also maintains the history of actual usage and details of number of cycles completed for output to a display for the user's records.

Another object of the present invention is to provide rapid transitions between temperatures for the most effective hot/cold cycle treatment. Once the desired temperature is reached, another object of the invention is to maintain the temperature without fluctuations or slow degradation.

In some embodiments, the device is lightweight, preferably under 15 lbs. excluding the power supply. It is preferably a single assembly that contains the controller, display, fan, TEM, thermal plate, and housing.

BRIEF DESCRIPTION OF THE DRAWINGS

FIG. 6 is a perspective view of the control unit end of the conduit;

FIG. 7 is front view of the end of FIG. 6;

FIG. 8 is a perspective view of the thermal garment end of the conduit;

FIG. 9 is a perspective view of the thermal end of the conduit in association with the port of the thermal garment;

FIG. 11 is a view of FIG. 4, now showing a message on its screen;

FIG. 12A is a top view of an exemplary thermal garment for wrapping a foot;

FIG. 12B is a perspective view of the garment of FIG. 12A showing the garment in use;

FIG. 149 is a perspective view of the garment of FIG. 14A showing the garment in use;

DESCRIPTION OF EMBODIMENTS

Certain embodiments of the invention are described blow. It should be understood that the invention is not limited to these exemplary embodiments.

Figure 1:
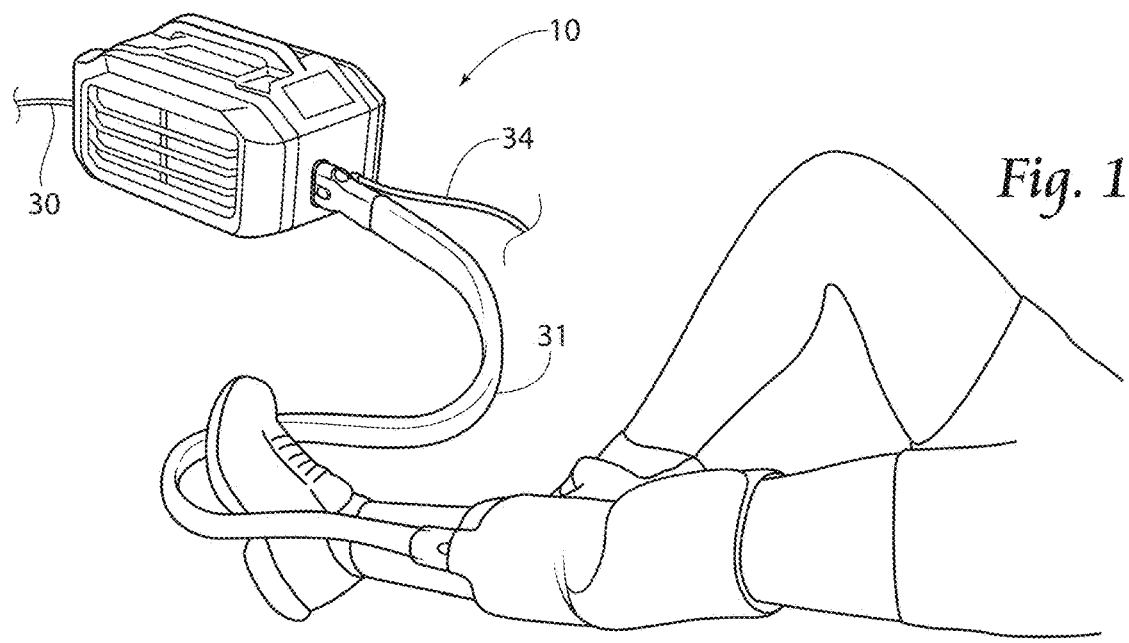
FIG. 1 is a perspective view of an embodiment of the system of the present invention, including a control unit, conduit, and thermal garment, shown in use.
Figure 2:
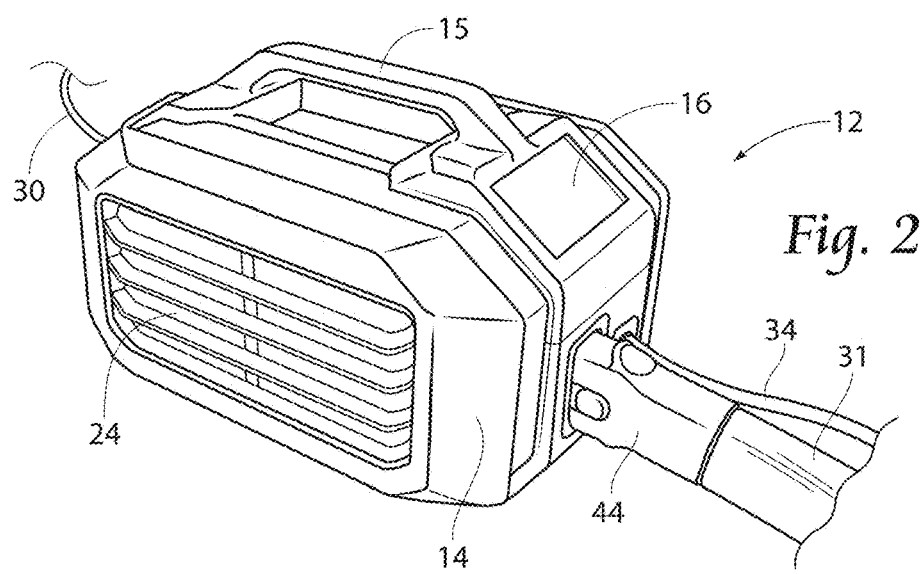
FIG. 2 is a front perspective view of the control unit of FIG.
Figure 3:
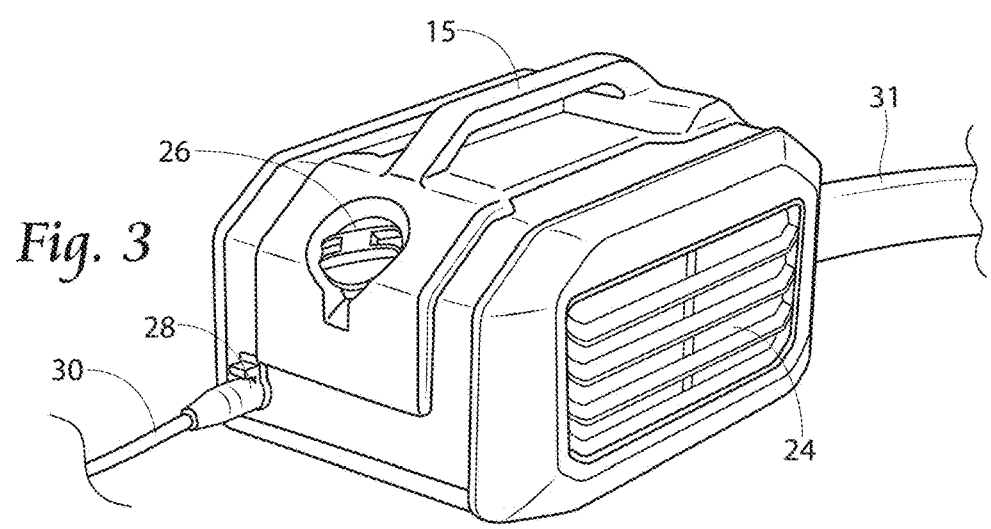
FIG. 3 is a rear perspective view of the control unit of FIG. 2.
Figure 4:
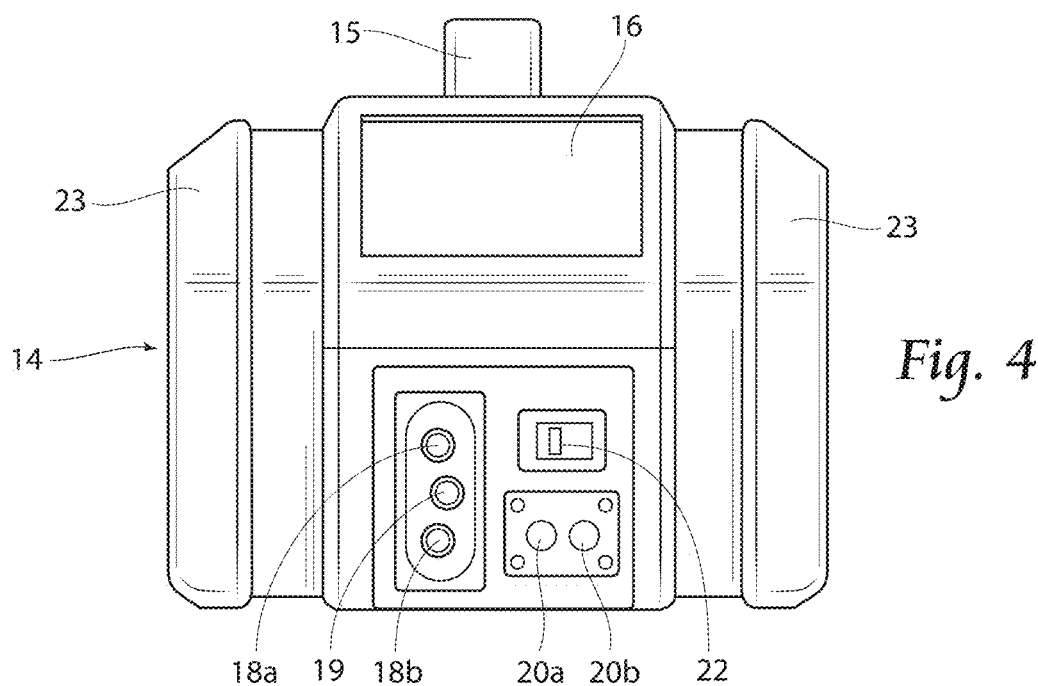
FIG. 4 is a front elevation view of the control unit of FIG. 2.

First describing the parts of system 10 generally, as seen in FIGS. 1-8, the present invention comprises a combination thermal compression and deep vein thrombosis prophylaxis compression device 12. Device 12 has a housing 14, preferably including an integrated top handle 15. Housing 14 includes a front section and a rear section and, as seen in FIG. 4, front section bears a screen 16, connection ports 18A, 18B, and 19, DVT ports 20a and 20b, and a USE port 22. USE port 22 is currently designed to charge a user's phone or other device, but could have multiple future applications. Further technologies may supplement or supplant a USE port without change to the scope of this patent application.

Note that connection port 19 is connected to the air pressure control system 100 to provide a garment with air pressure, thus providing the opportunity to provide both temperature and pressure therapy with a single garment. Housing 14 further includes a pair of sides bearing side vents 24, and rear section bearing a fluid tank cap 26 and an electrical cord port 28 into which a desktop power supply cord 30 may be inserted.

System 10 also has a thermal connection hose 31 that is connectable to thermal garments 32, and DVT lines 34 that are connectable to separate DVT-only compression garments 36.

Figure 5:
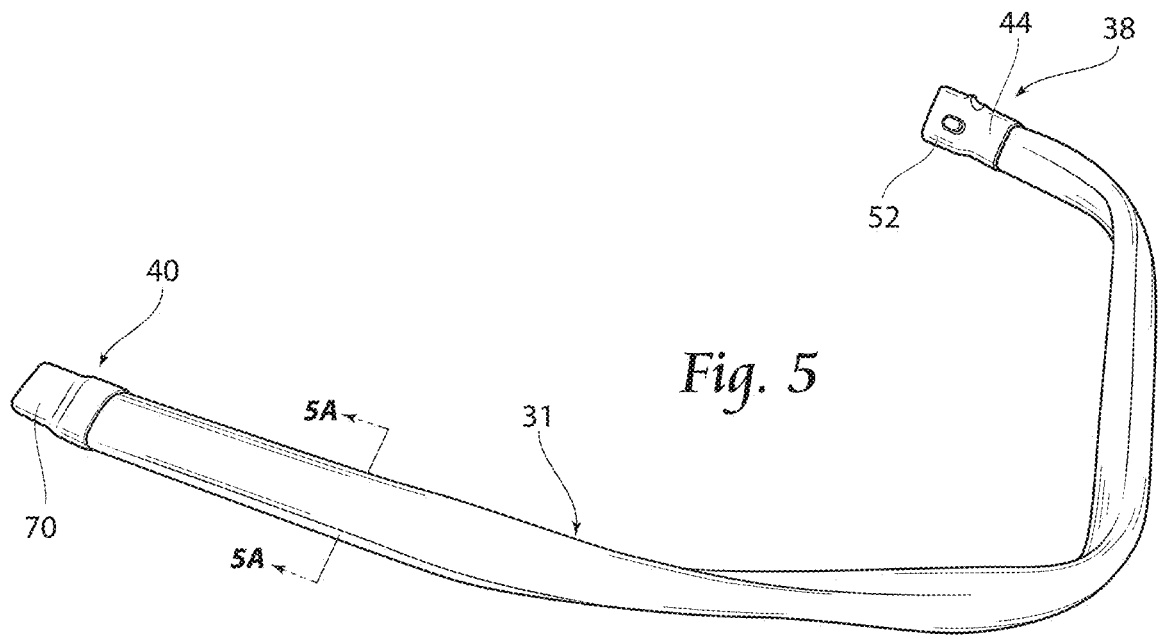
FIG. 5 is a perspective view of the conduit shown in FIG. 1.
Figure 5A:
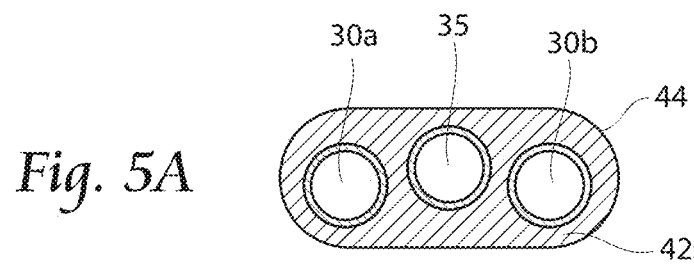
FIG. 5A is a cross-sectional view of the conduit of FIG. 5 taken from line 5A-5A.

Thermal connection hose 31, as shown in FIG. 5, has a device connector end 38 and a garment connector end 40. FIG. 5A shows that hose 31 contains conduits 30A, 30B, and 35 corresponding, respectively, to connection ports 18A, 18B, and 19. Conduits 30A and 30B transport fluid to and from garment 32, while conduit 35 provides air to inflate garment 32. Conduits 30A, 30B, and 35 are contained within an insulating sheath 42 that minimizes temperature changes to fluid contained in conduits 30A, 30B by way of ambient temperature.

As can be seen in FIG. 6, device connector end 38 has a shell 44, preferably made of a heavy duty plastic, through which conduits 30A, 30B, and 35 connect with device 12. Shell 44 has a front end 46 with connection mounts 48 extending therefrom, an aperture 50 through which a disconnect button 52 extends, and a thumb structure 54.

Connection mounts 48 are retained in connection ports 18A, 18B, and 19 by way of corresponding retention tabs 58 and retention catches 60 (not shown in present draft drawings) that connect with one another by inserting shell 44 into ports 18A, 18B, and 19, optionally using thumb structure 54 to assist in a firm connection. To disconnect, pressing button 52 retracts retention tabs 58 so that shell 44 may be removed from ports 18A, 18B, and 19.

Garment connector end 40 terminates in a garment connection shell 70 constructed of a hard plastic material or the like. Shell 70 contains fluid conduit outlets 74A and 74B as well as air outlet 75.

On the garment side, as shown in FIG. 8, garment inlet shell 72, again preferably constructed of a durable material such as hard plastic, contains inlets 76A, 76B, and 77 corresponding to conduits 74A, 74B, and 75. Accordingly, garment connection shell 70, when properly coupled with garment inlet shell 72, establishes a mating communication between outlets 74A, 74B, 75 and inlets 76A, 76B, 77.

The connection between shell 70 and inlet shell 72 is firmly established by way of a mechanical catch (not shown) and is releasable by a release button 80.

Note that DVT pressure can be applied without temperature treatment. As seen in FIG. 4, a set of ports 20a, 20b is provided apart from thermal connection hose 31 and its associated ports 18a, 18b, 19.

DVT lines 34, which are preferably made of polyurethane but can be constructed of any other appropriate material, and may be connected to DVT ports 20a, 20b by way of a press fit or any other appropriate connection type. As seen in the drawings, a press fit is accomplished using an O-ring or the like (not shown) within DVT ports 20a, 20b or on the outer diameter of DVT lines 34.

Either a single port may be connected to provide compression therapy via a single DVT garment 36, or both of ports 20a, 20b may be used simultaneously or cyclically in connection with two compression garments 36. In the embodiment shown in FIGS. 1 and 2, only one DVT line 34 is shown connected to either port 20a or 20b, either of which may be used without the other.

Turning to FIG. 4, screen 16 displays messages relating to the programming and status of device. For example, as seen in FIG. 11 at the start of a thermal cycle, screen 15 may provide cycle or program choices. During a cycle, device status error messages could appear. An exemplary error message might read: "ALERT! Garment or hose is not firmly attached. Rewrap garment and reattach hose connection until a 'click' is heard."

Heat Exchanger ("Chiller Block") with Dual TEMs

As shown in FIGS. 21-24 and 31-34, system 10 (see FIG. 1) of the present invention includes a chiller block 100 that is comprised of a stack of three plates 102 arranged atop one another rather than within the same plane. This arrangement provides for increased thermal performance and requires no external cooling fins or other structures reliant on ambient air.

Chiller Block 100 further comprises a pair of thermoelectric modules (TEMs) 704. TEMs are solid-state heat pumps composed of two ceramic substrates that serve as electrically insulating materials and house P-type and N-type semiconductor elements. Heat is absorbed at the cold junction by electrons as they pass from a low-energy level in the P-type element onto a higher energy level in the N-type element. At the hot junction, energy s expelled to a thermal sink as electrons move from a high energy element to a lower energy element.

When DC current flows through the TEMs, heat transfer creates a temperature differential across the ceramic surfaces. As such, one side of the TEM is cold while the other side is hot. Reversing the polarity of the current changes the direction of heat transfer thus reversing the cold side to the hot side and vice versa.

Figure 32:
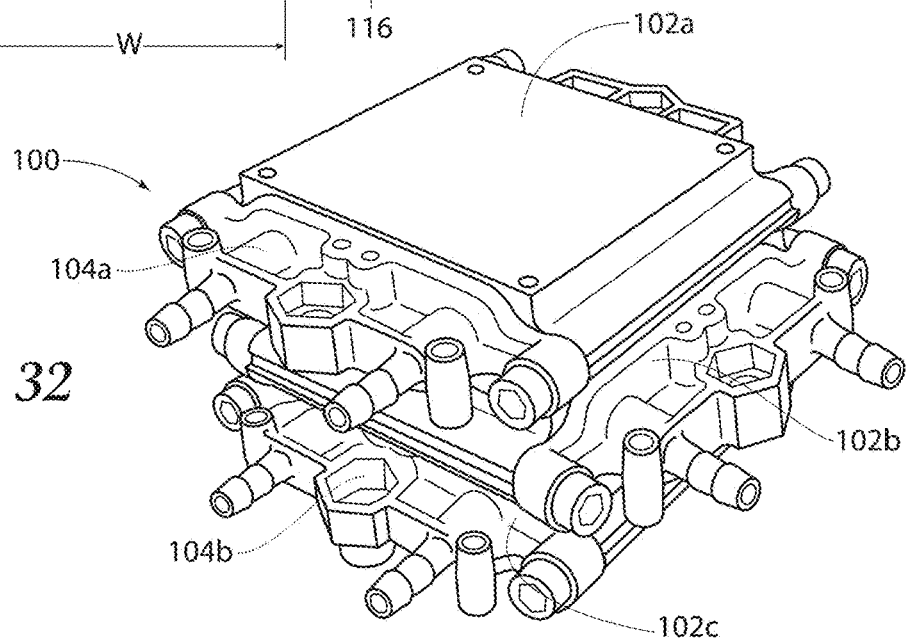
FIG. 32 is a perspective view of the plates of the chiller block stacked for assembly.
Figure 33:
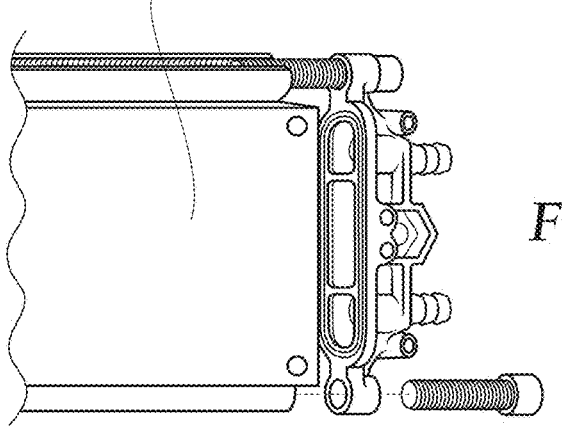
FIG. 33 is a view of an endcap being attached to a chiller block plate.
Figure 34:
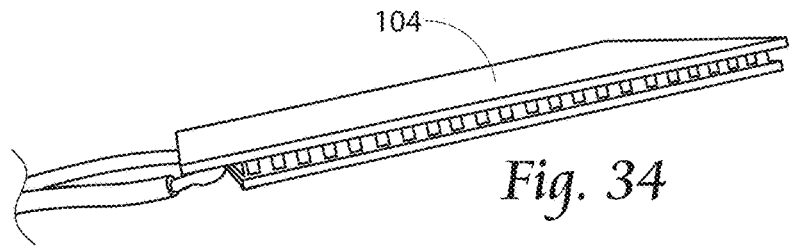
FIG. 34 is a side view of the thermoelectric module.
Figure 35A:
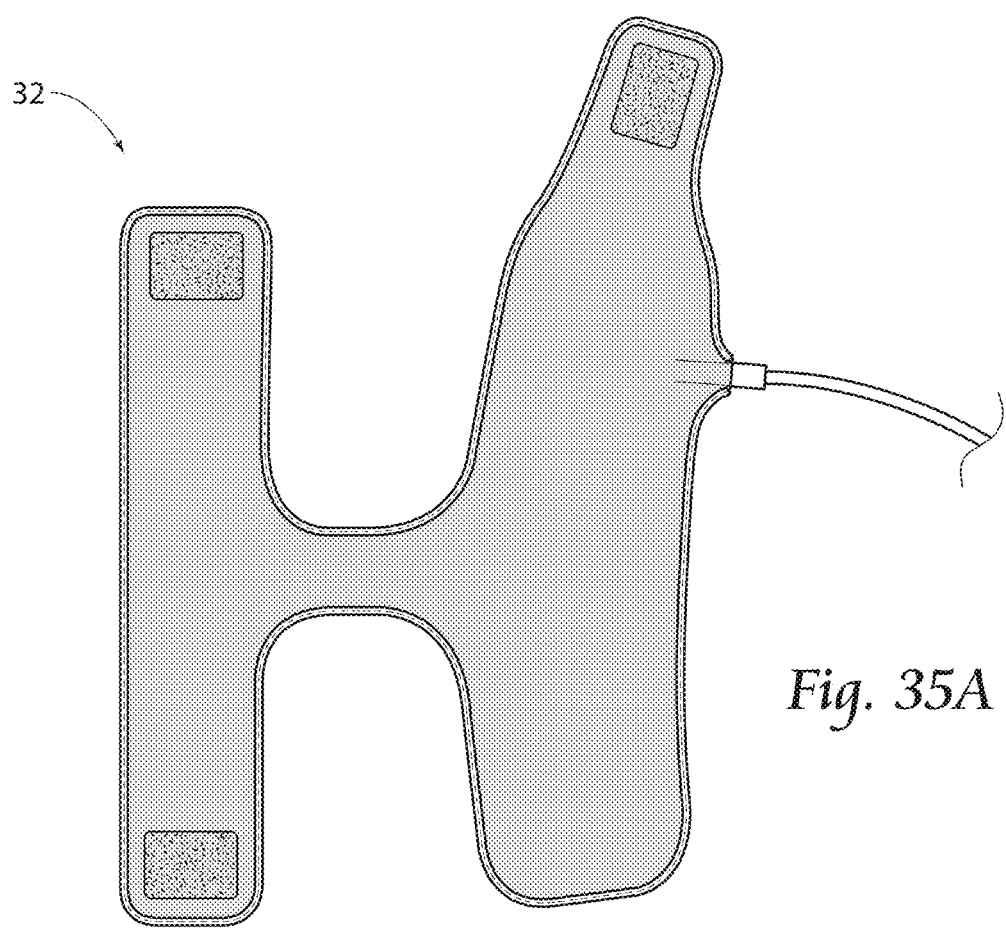
FIGS. 35A and 35B are laid-open and in-use views of a DVT ankle garment.
Figure 35B:
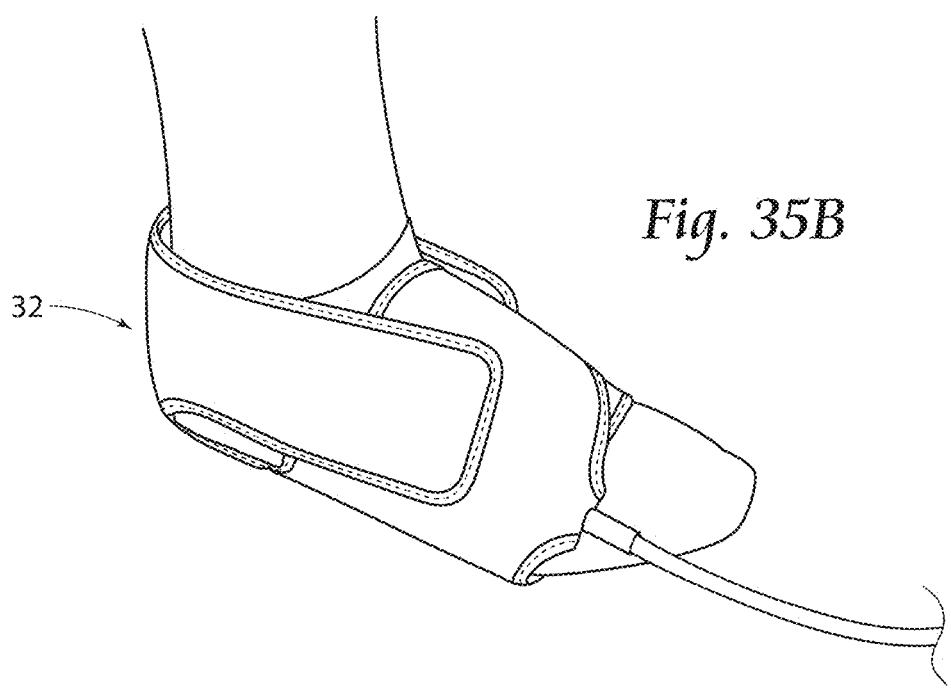
Figure 36A:
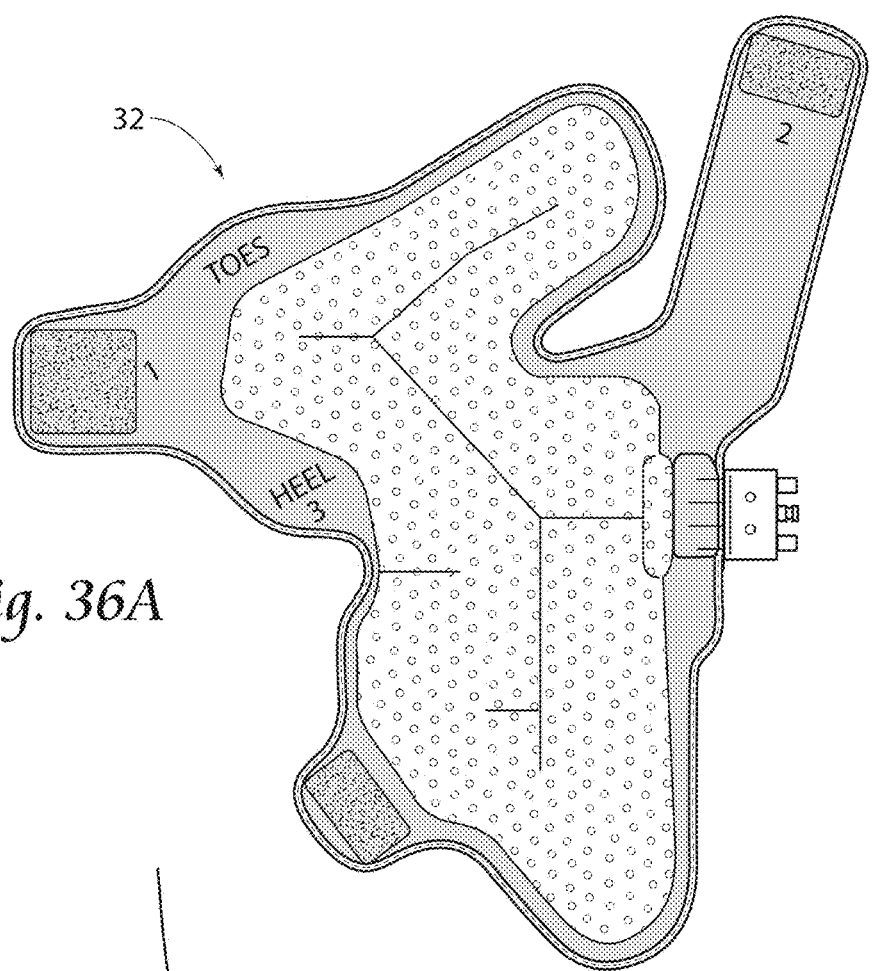
FIGS. 36A and 36B are laid-open and in-use views of a thermal ankle garment.
Figure 36B:
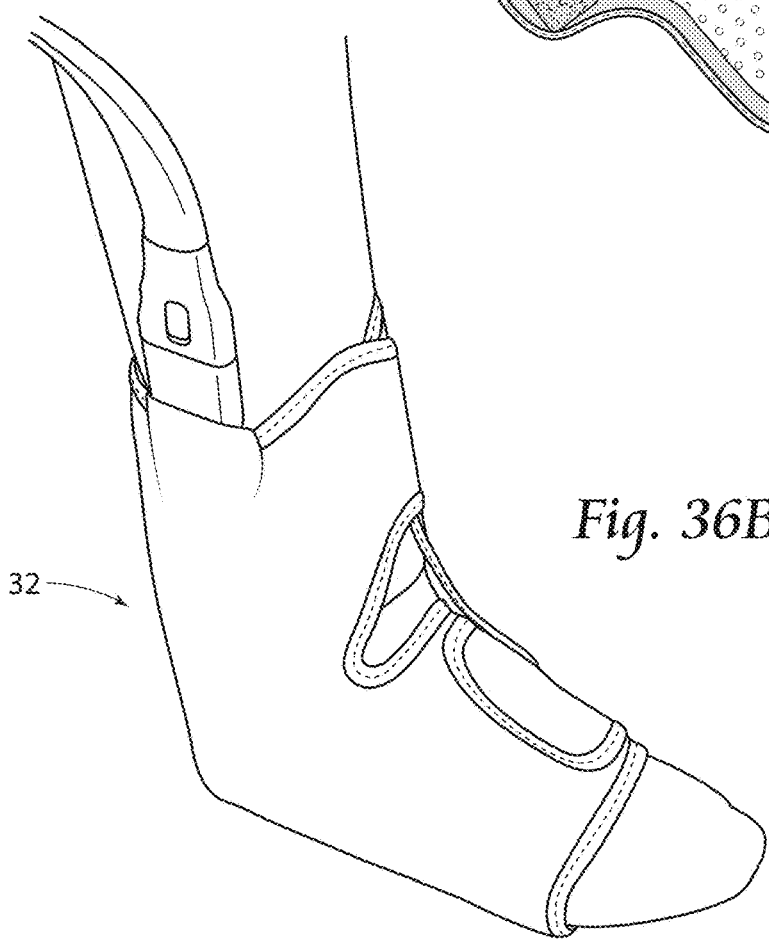
Figure 37A:
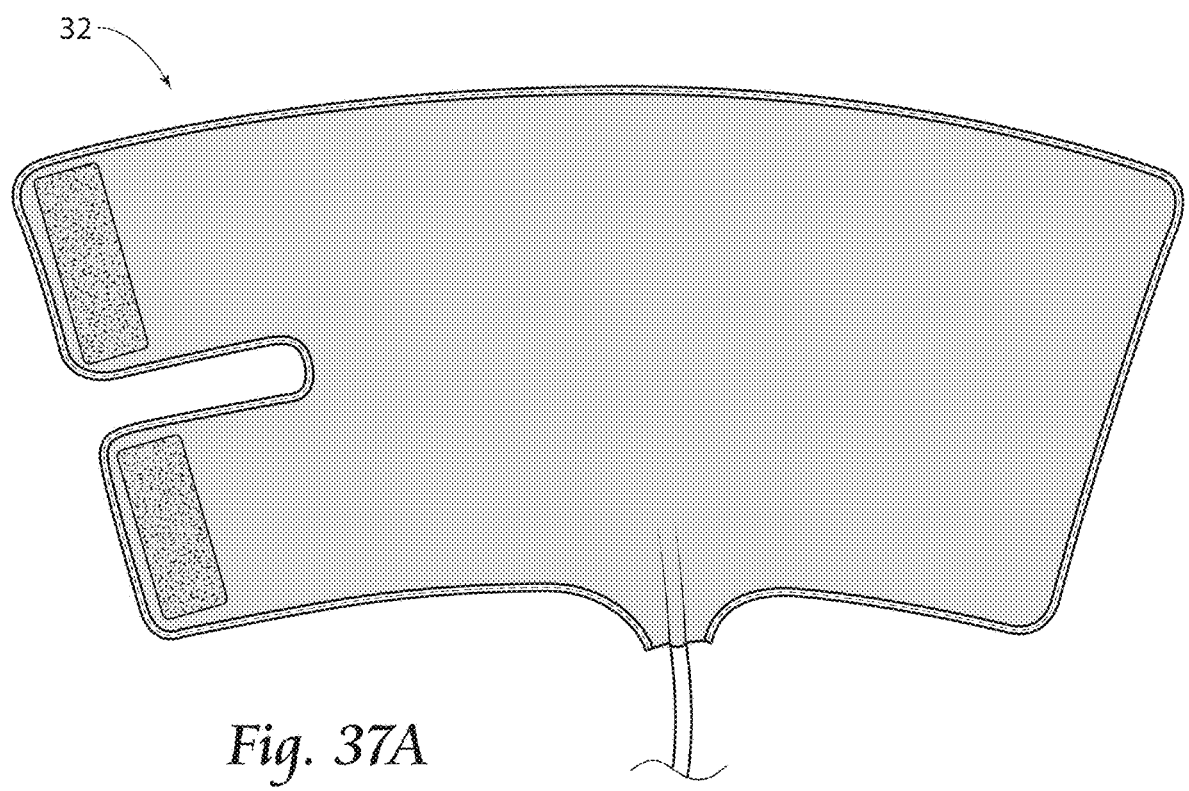
FIGS. 37A and 37E are laid-open and in-use views of a DVT calf garment.
Figure 37B:
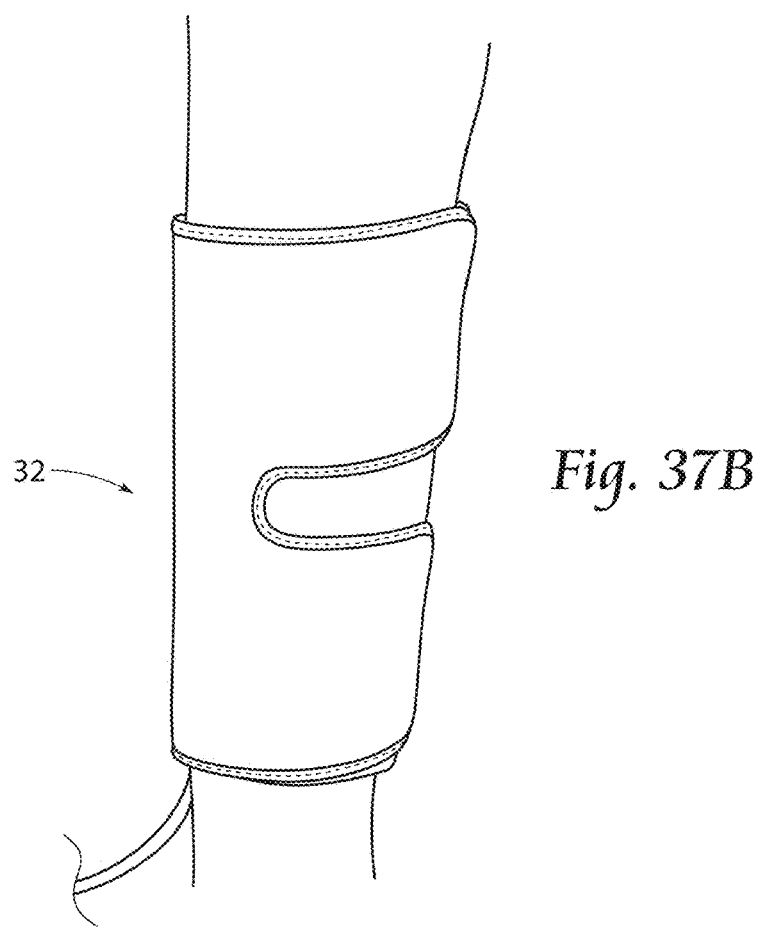
Figure 38A:
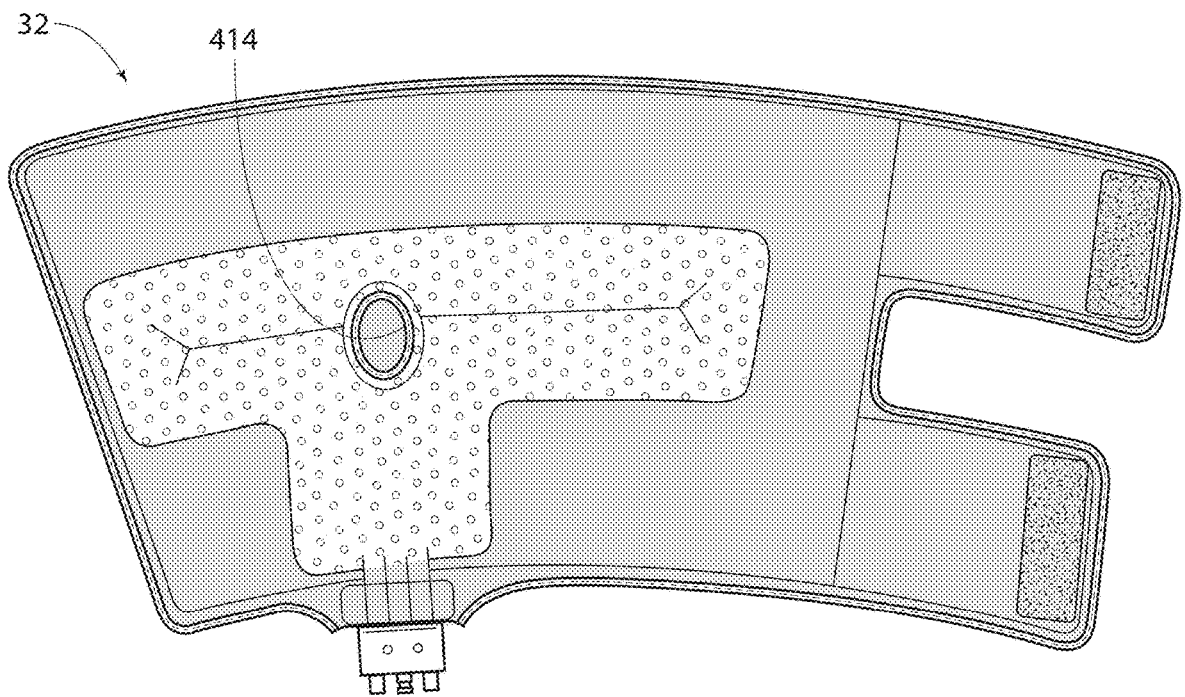
FIGS. 38A and 38B are laid-open and in use views of a thermal knee garment.
Figure 38B:
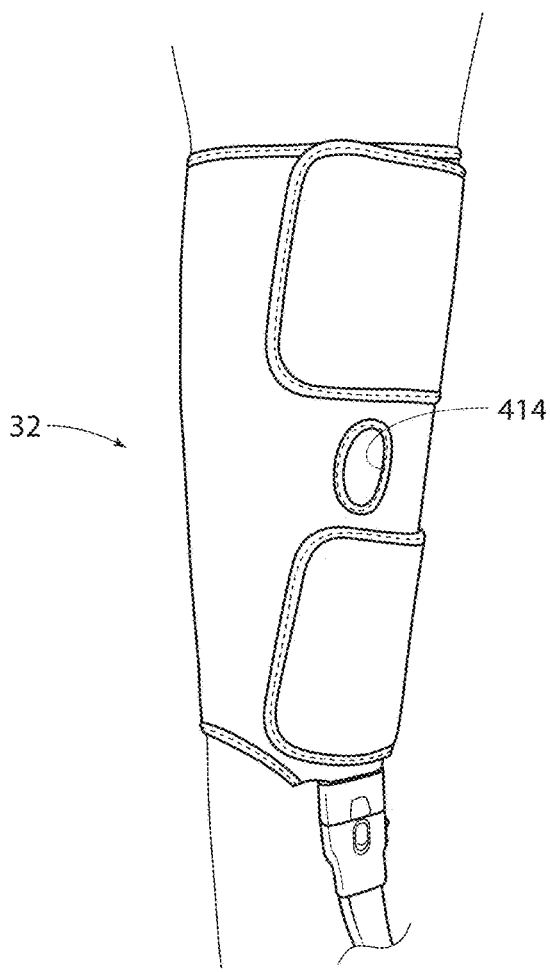
Figure 39A:
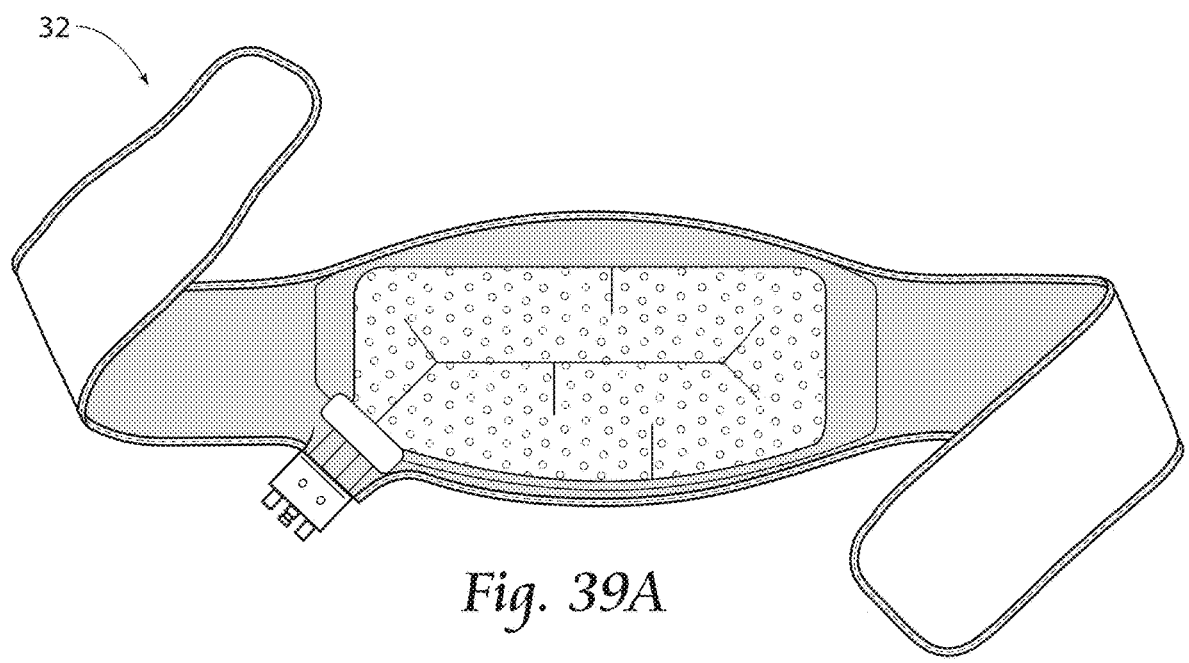
FIGS. 39A and 39B are laid-open and in-use views of a thermal back garment.
Figure 39B:
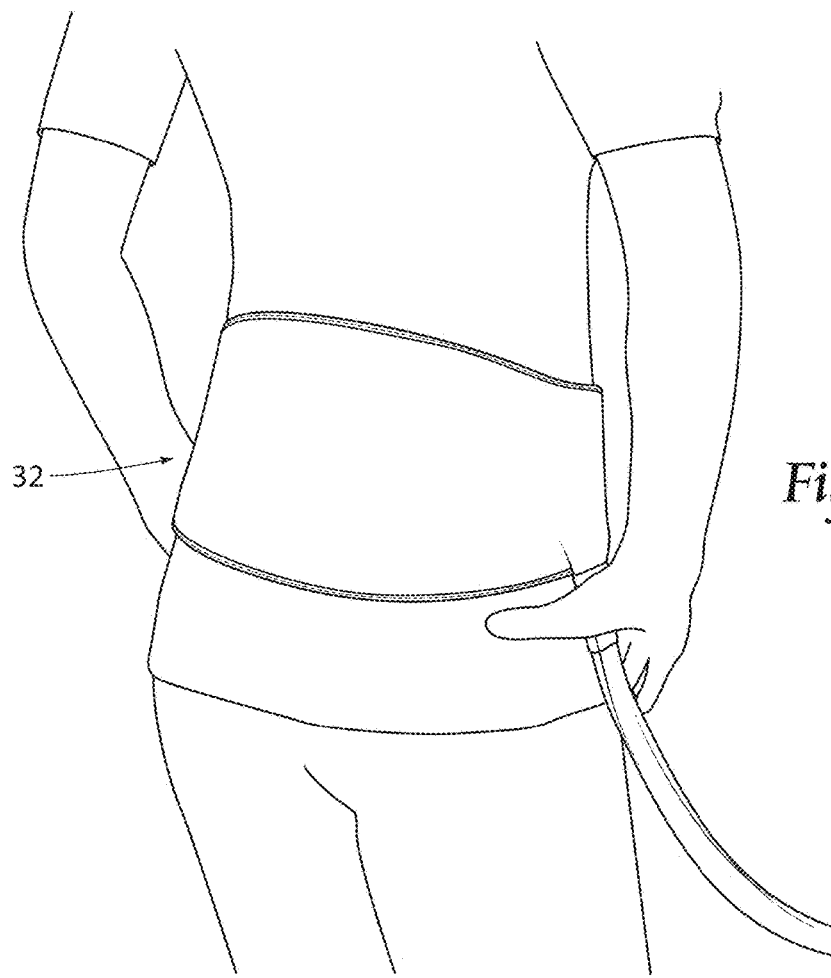
Figure 40A:
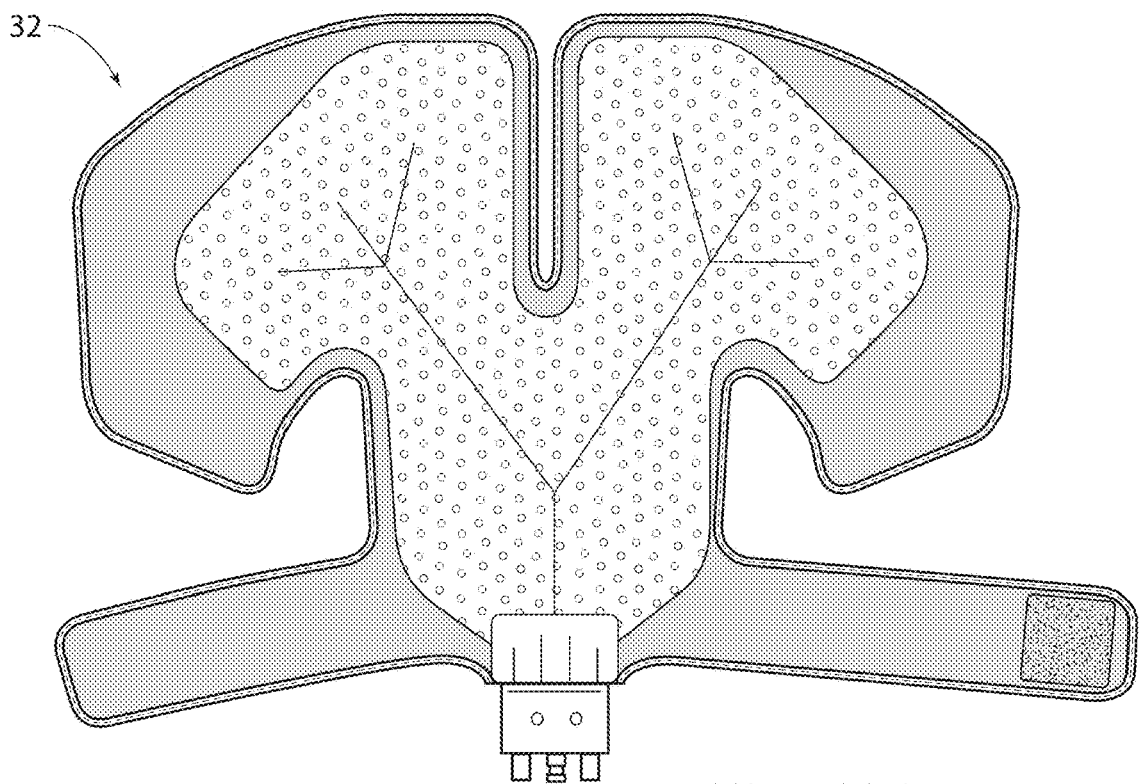
FIGS. 40A-40D are laid-open and in-use views of a thermal shoulder garment.
Figure 40B:
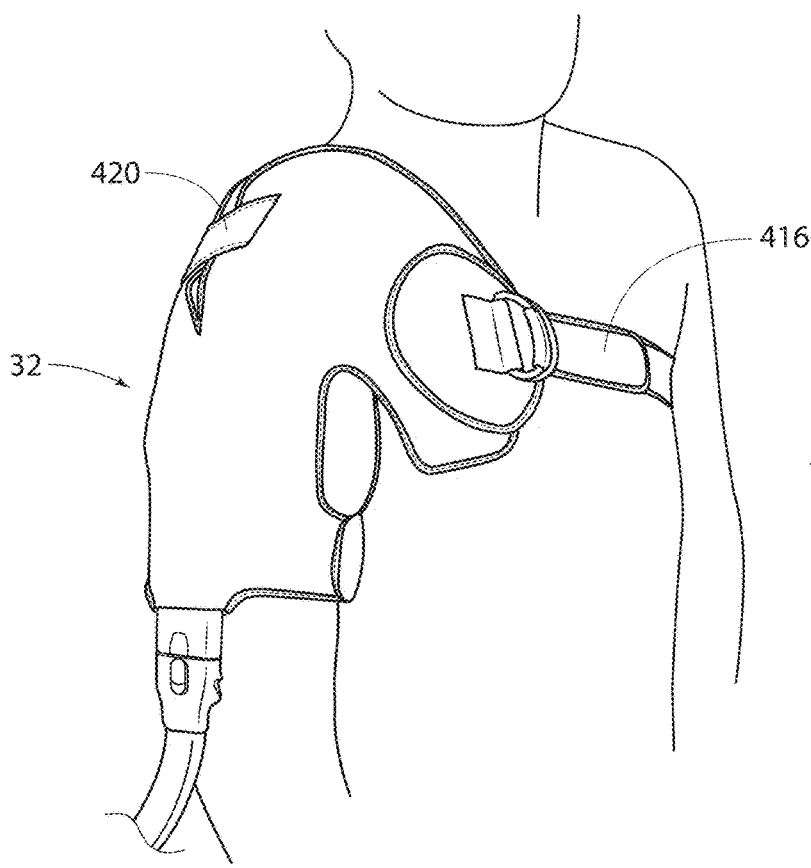
Figure 40C:
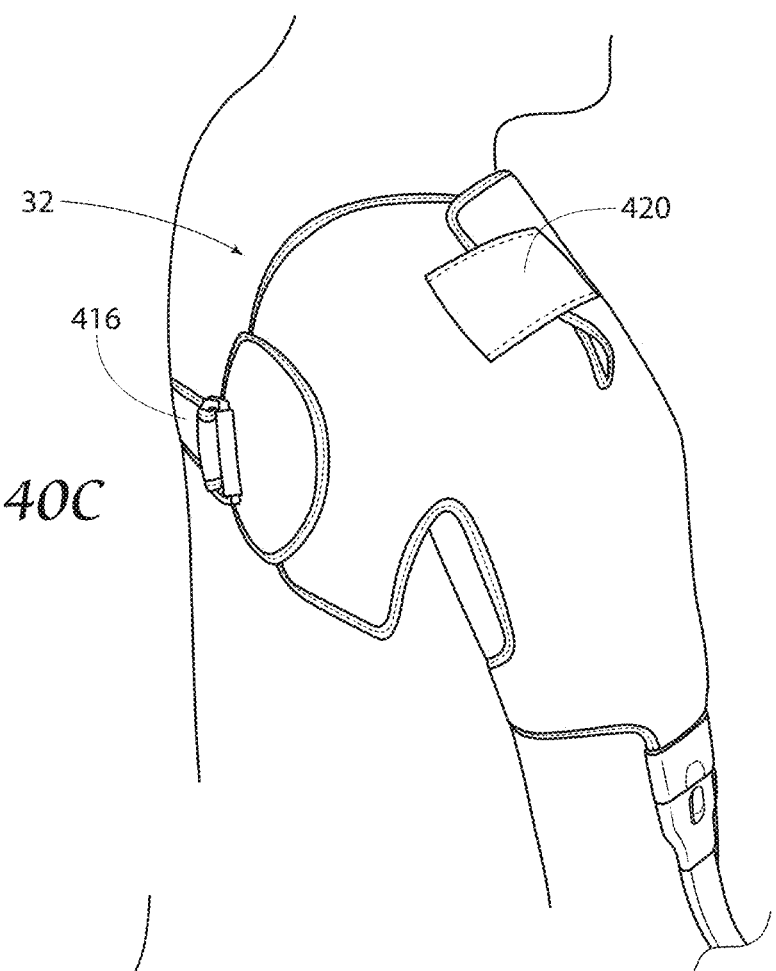
Figure 40D:
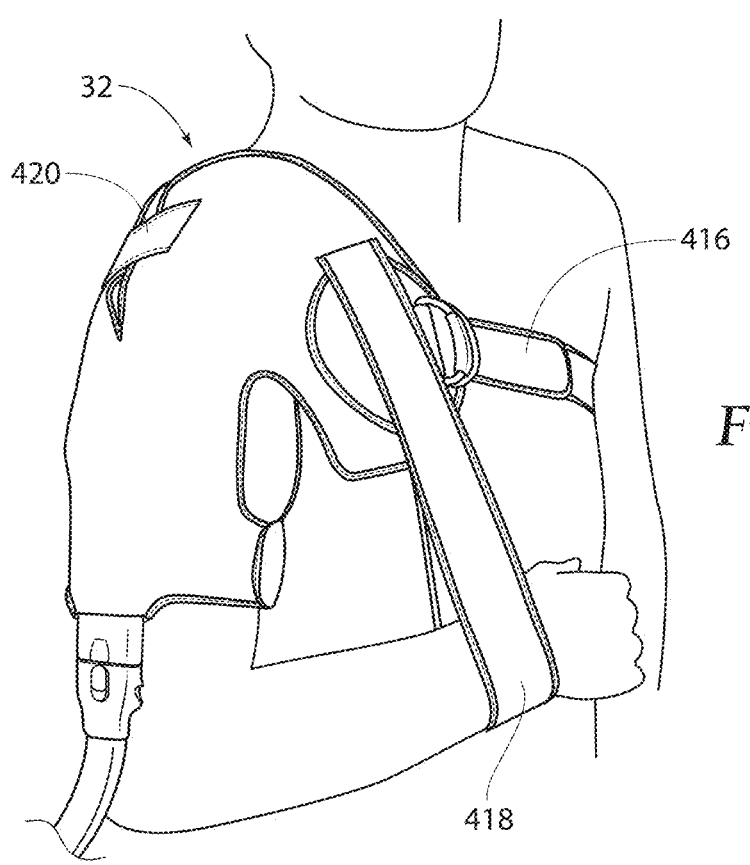
Figure 41A:
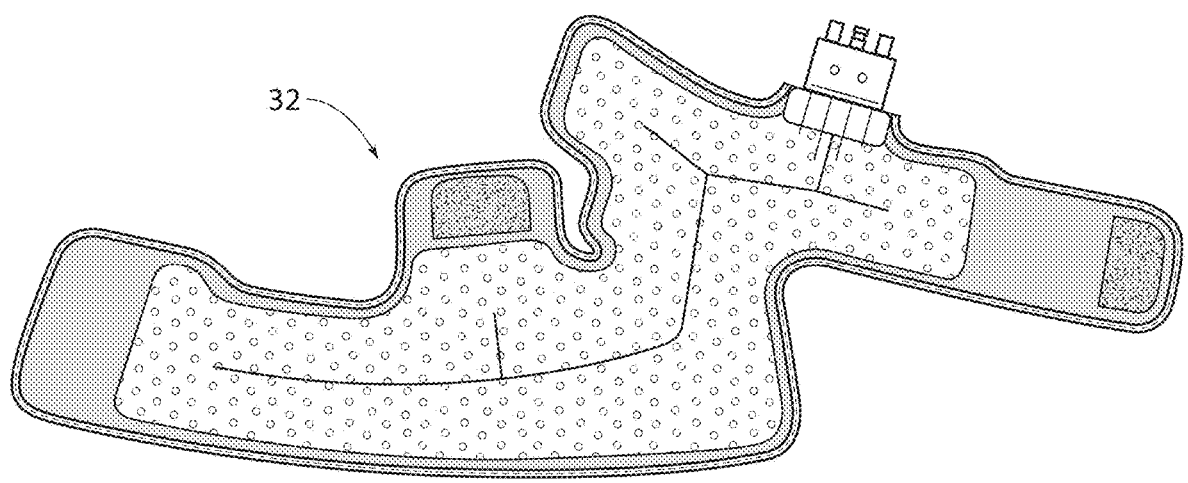
FIGS. 41A and 41B are laid-open and in-use views of a thermal elbow garment.
Figure 41B:
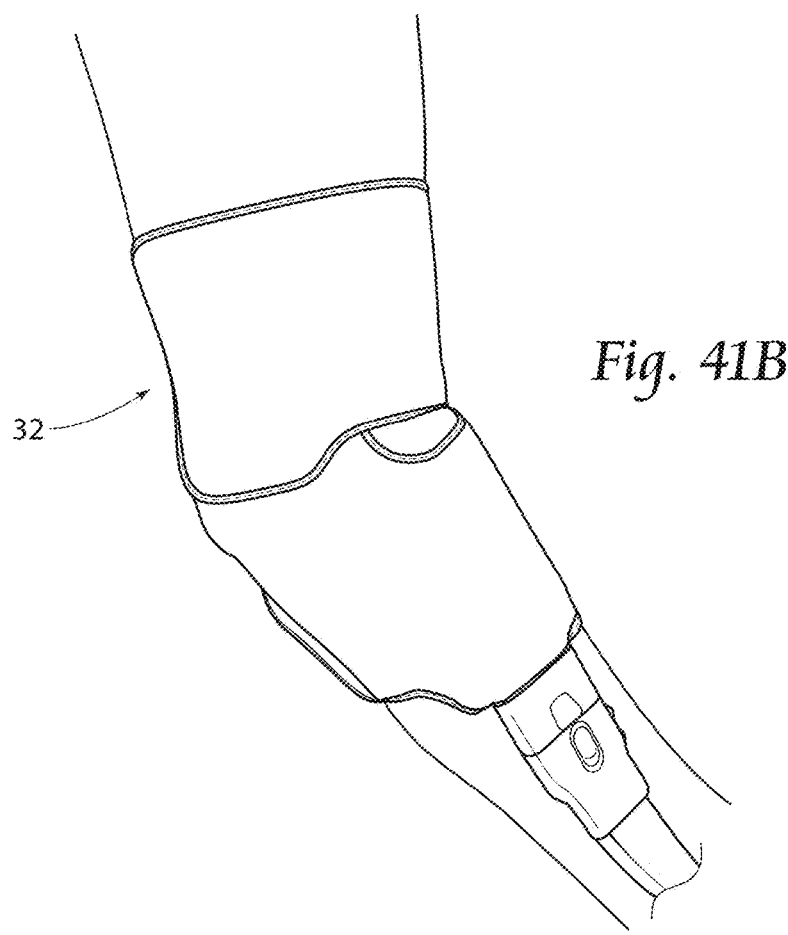

In the present invention, TEMs 104 are used to heat or cool the fluid of system 10 by arranging plates 102 and TEMs 104 in an alternating fashion to create chiller block 100. As seen in FIG. 32, plates 102 are stacked one on the other with the center plate 102b being rotated 90° from the top and bottom plates 102a, 102c. Not seen are TEMs 104 located between plates 102. However, the chiller block is stacked as follows: top plate 102a, first TEM 104a, center plate 102b, second TEM 104b, and bottom plate 102c.

Plates 102 are preferably made of aluminum for cost and weight reduction. They are also preferably identical to one another to reduce machining costs.

In the present embodiment, each of plates 102 has 36 bores 106 passing through its width. Bosses 106 have a preferred inner diameter of 0.067" and are created by a process utilizing drilling, electrical discharge machining, or any other suitable process. Naturally, the number and size of bores 106 can vary without changing the scope of the invention whatsoever.

Plates 102 have a top face 108 and bottom face 110, an inlet/outlet cap 112, and an endcap 114. Thumb screws 116 are provided for attaching caps 112, 114 to chiller block 100. Plates 102 have identical sides 118. Each of inlet/outlet cap 112 and endcap 114 has an opening 120 for a hex nut connection. A screw 121 and hex nut (not shown) are used to firmly connect plates 102a, 102b, 102c of chiller block 100.

Figure 25:
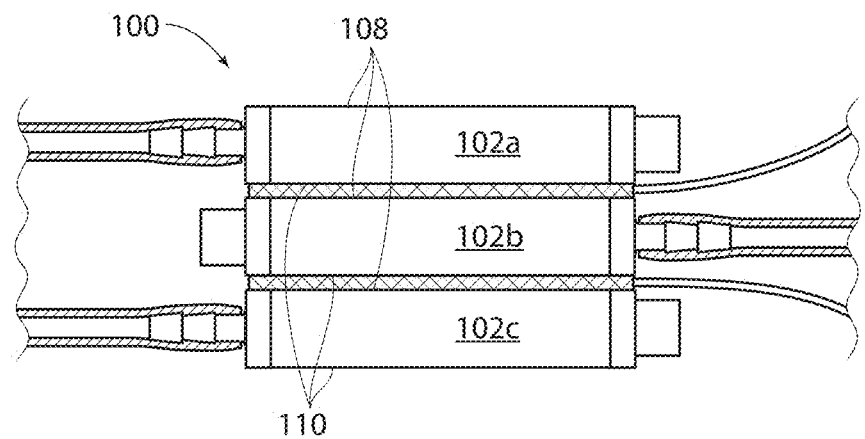
FIG. 25 is a side view of a chiller block showing placement of the thermoelectric control units between the plates, and related connection ducts and wires.
Figure 26:
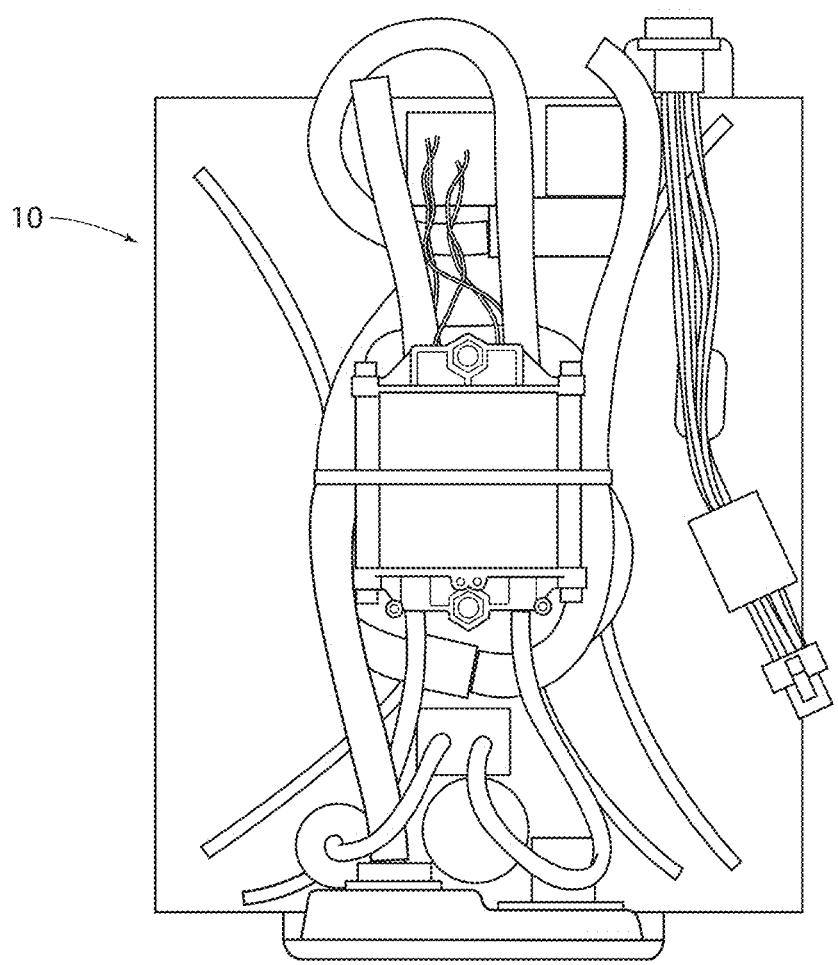
FIG. 26 is a top view of the interior of the control unit.
Figure 27:
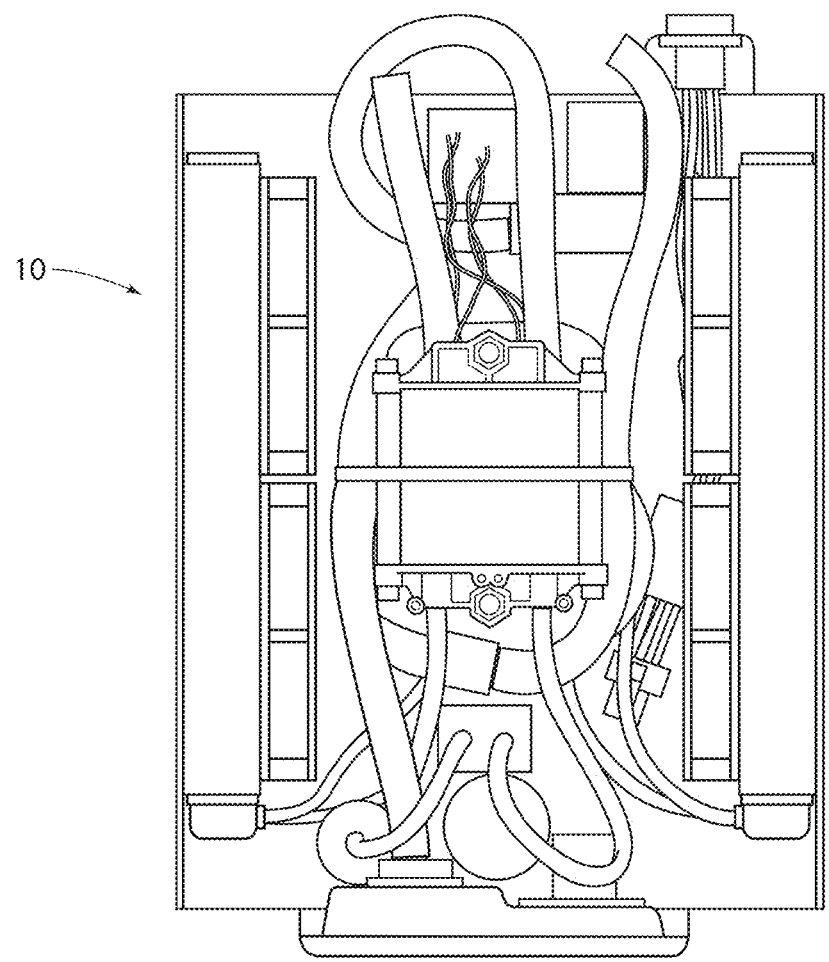
FIG. 27 is a top view of the interior of the control unit, now showing side frames.
Figure 28:
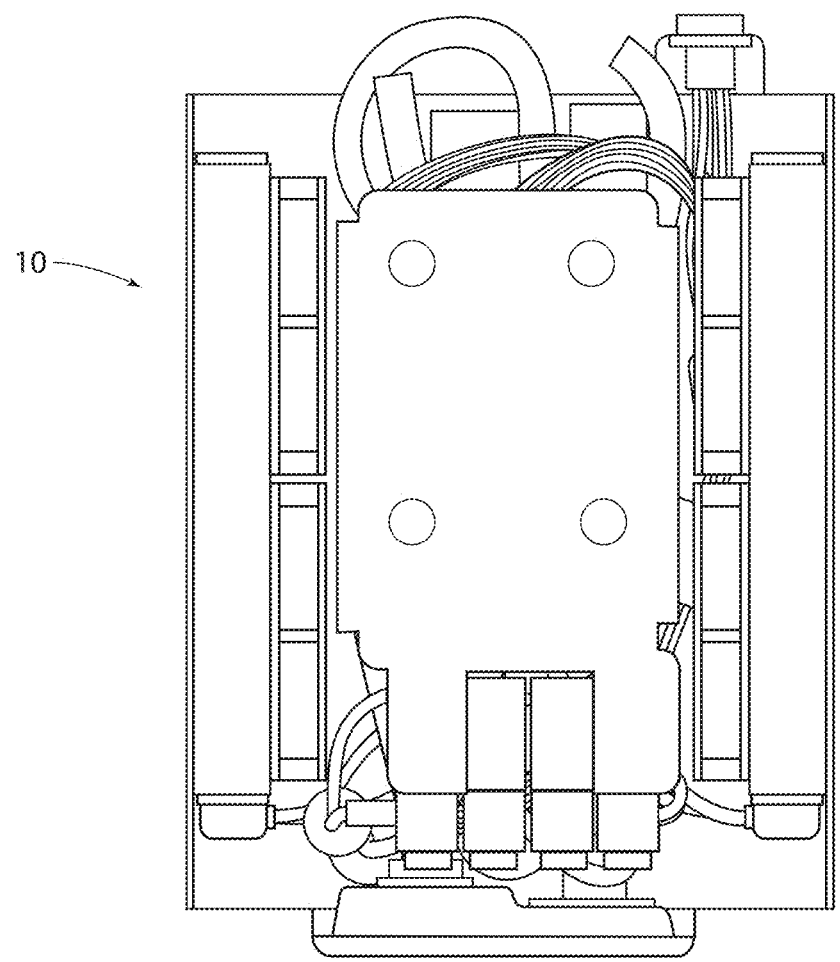
FIG. 28 is a top view of the interior of the control unit, now showing a top plate.
Figure 29:
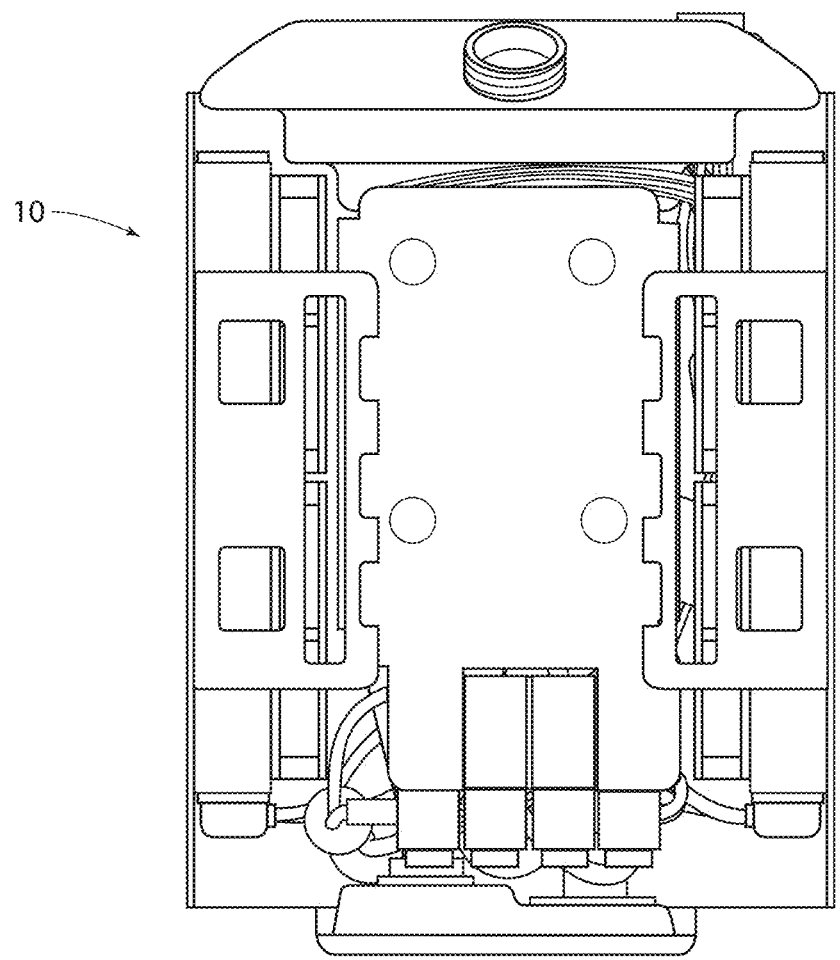
FIG. 29 is a top view of the interior of the control unit, now showing top plate frames and the fluid tank.
Figure 30:
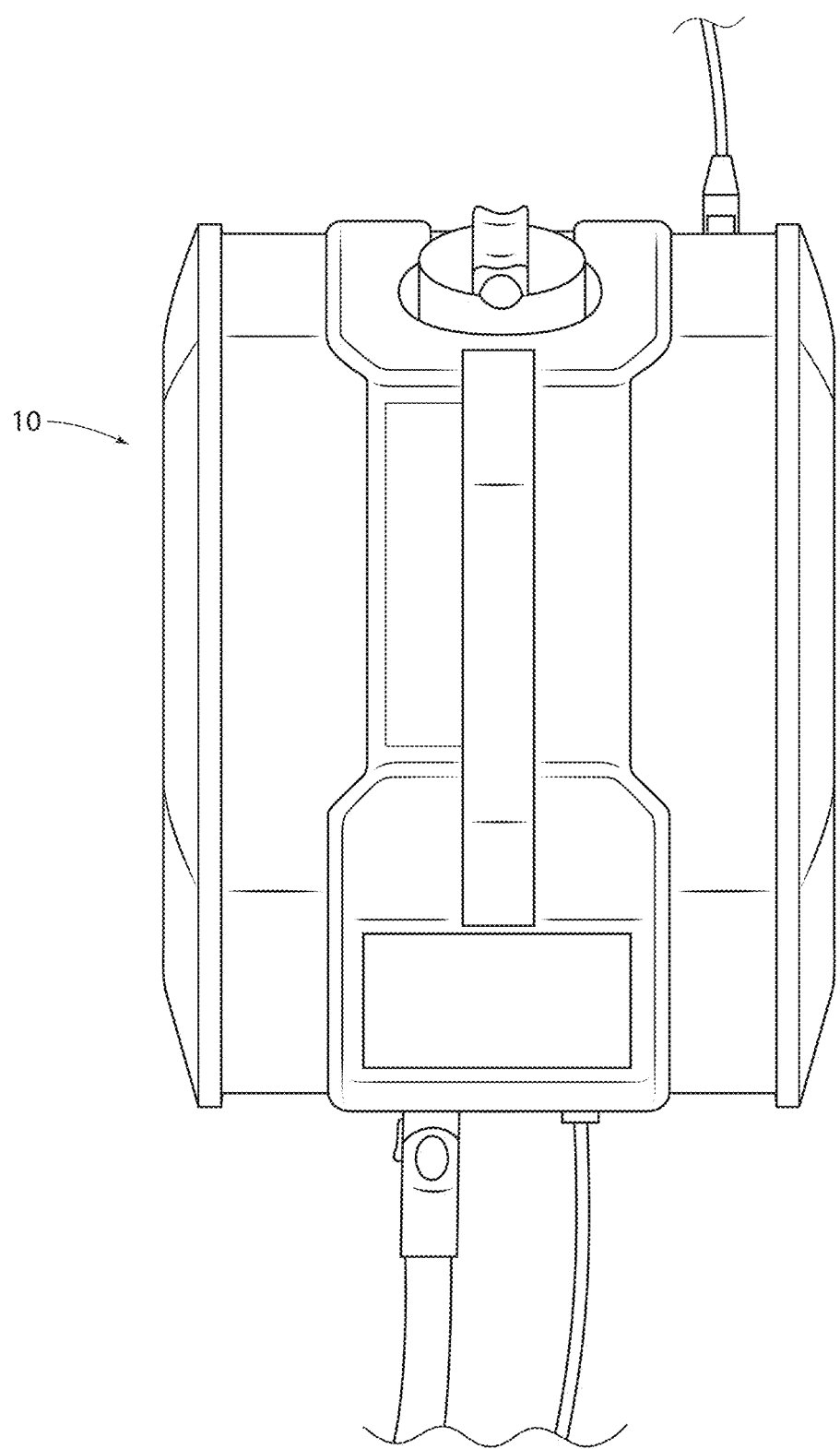
FIG. 30 is a top view of the control unit, now showing the housing therefor.

As seen in FIG. 25, each of plates 102a, 102b, and 102c is stacked axially with top plate 102a and bottom plate 102c facing in one direction, and center plate 102b turned 180 degrees axially from the orientation of the top and bottom plates 102a, 102c. A 90 degree turn could also be employed.

Figure 31:
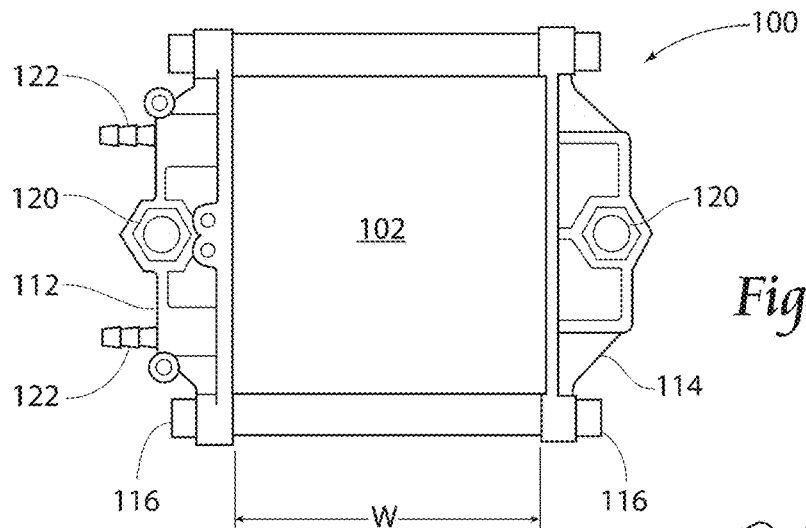
FIG. 31 is a top view of a plate of the chiller block.

Turning to FIG. 31, each inlet outlet cap 112 bears a pair of nipples 122 which deliver fluid to and from an associated plate 102 of chiller block 100. The fluid is directed through the plate 102 so that it is required to pass through bores 106, extending the width of plate 120, four times. This gives plates 102 and bores 106 adequate exposure to the heat or cold provided by TEM 104 so that the fluid is likewise heated or cooled. Multiple passes through plate 102 provides efficient adjustment of fluid to the desired temperature.

Figure 23:
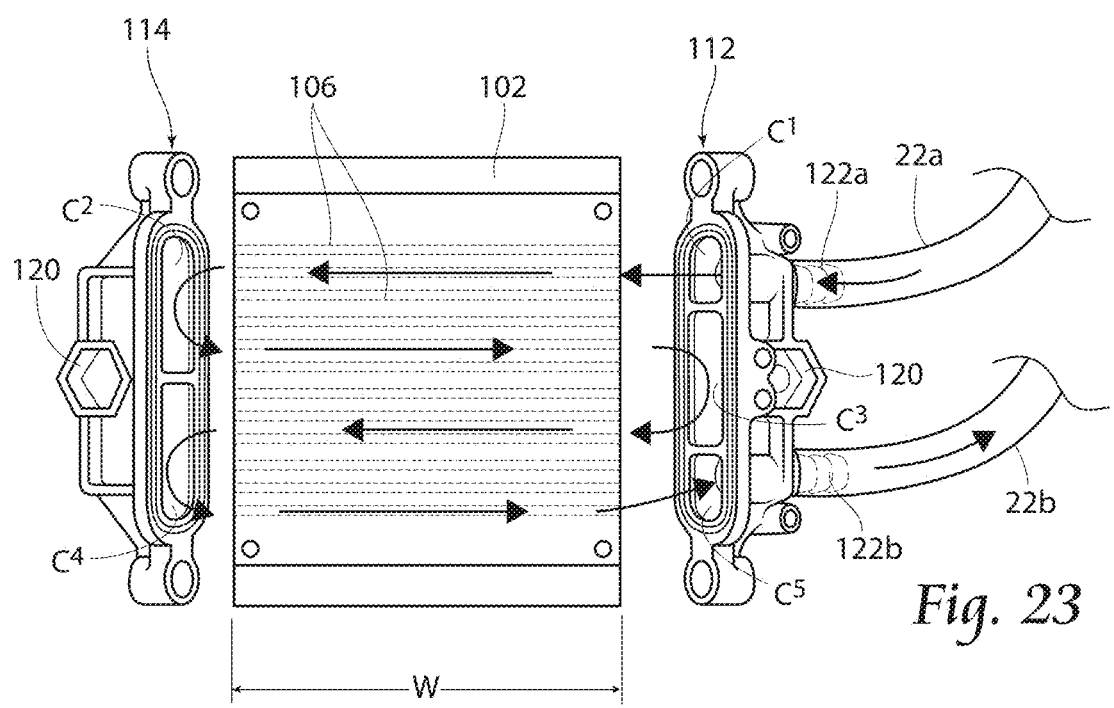
FIG. 23 is a top view of a plate of a chiller block of the embodiment illustrating the air flow pattern between the fluid system and thermoelectric control unit and, in dotted lines, bores therethrough.
Figure 24:
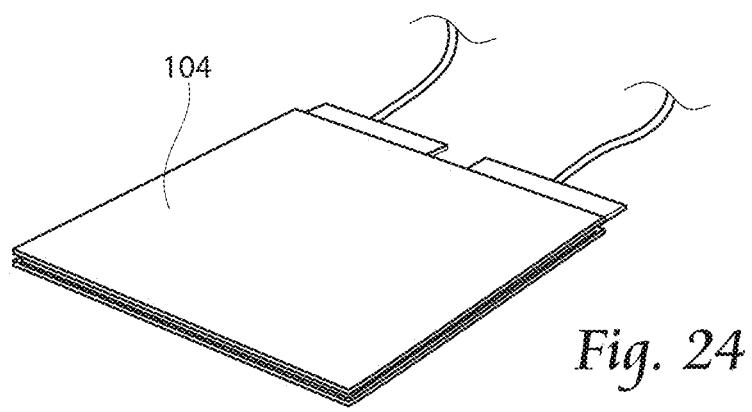
FIG. 24 is a perspective view of a thermoelectric control unit.

Specifically, referring to FIG. 23, thermal conduits 22A and 22B attach to nipples 122A and 122B via friction fit. Nipples 122A deliver fluid of the system into inlet/outlet cap 112 through openings 112A. Openings 112a are surrounded by a raised perimeter creating a first chamber (C1). The fluid passes through chamber C1 through connected bores 106. The fluid exits the bores 106 of chamber C1 at a second chamber C2 of endcap 114, and is redirected back toward inlet/outlet cap 112 via return bores 106. The fluid then enters and subsequently exits chamber C3, flows back to endcap 114 to chamber C4, and then to chamber C5 where it returns to system 10 via nipple 122B.

Plates 102 of the preferred embodiment, as well as related parts and functions, have been described herein. However, numerous variations on each of these details are possible and all should be considered within the scope of the invention.

The other primary components of chiller block 100 are a pair of thermoelectric modules (TEMs) 118. One of each TEM 118 is placed between top plate 102a and center plate 102b, and the other between center plate 102b and bottom plate 102c.

Series/Parallel TEM Control

TEMs are frequently used with a control mechanism to regulate the temperature of a medium being heated or cooled. Control mechanisms include pulse width modulation (PWM) of the power to the device, changing the DC voltage the TEM is driven by, or a simple on/off power control.

PWM control comprises or consists of changing the percent of time in each cycle that the device is either on or off. For example, with a 100 Hz frequency, the device can be turned on anywhere from 0 to 100% duty cycle to control the amount or heat energy the device moves, up to the limit the TEM achieves on direct current.

Using a PWM duty cycle less than 100% has the same effect on the TEM as lower DC voltage. As such, PWM is an effective control strategy, when used with temperature feedback, to control the temperature of the medium that is heated or cooled.

The disadvantage of using PWM is that it generates a high level of radio frequency (RF) noise since the TEM current is switched on and off many times per second. Such high RF noise is unacceptable in medical devices, particularly in life-maintaining medical devices, in which RF noise can interfere with proper operation.

Changing the TEM power supply DC voltage, used in conjunction with temperature feedback, is also an effective control strategy. This gives fine control over the medium temperature, since the TEM is primarily a resistive device and responds to changes in supply voltage. However, controlling the voltage output of a DC power supply also normally involves changing the PWM switching internal to the supply itself at a very high frequency. This also generates a high level of RF noise.

True analog control DC power supplies that do not use PWM for voltage control are normally reserved for laboratory use since they are very big, bulky, and expensive to manufacture.

Simple on and off control of the power to the TEM at a slow (less than 1 second cycle time) rate does not generate high levels of RF noise, but can shorten the life of the TEM from thermal fatigue. It also gives a highly inaccurate temperature control scheme with under- and overages. As such, it is not suitable for applications with fine control requirements such as medical devices.

Since the TEM current required at a fixed voltage is also dependent on the temperature differential across the TEM, the on/off method requires more electrical power from the power supply to be able to supply the high current requirements every time the TEM is turned on and off. Turning the TEM on and off at a slow rate allows the temperature differential built from operation to dissipate, causing the subsequent turn on to require more starting power and thermally fatigues the TEM.

The method of the present invention comprises a method of controlling a device in which more than one TEM is utilized. Multiple TEMs can either be connected in a series or parallel configuration, depending on the application and the specific power supply.

One example of keeping power supply voltages and TEM characteristics the same comprises using a parallel connection. The main supply voltage is applied to both TEM elements and doubles the current requirement from the power supply.

Series connection divides the supply voltage to each TEM in half, and also essentially doubles the resistance of the load and cuts the power supply current delivery in half.

Thus, in a parallel connection arrangement, each TEM works at "full power" in a parallel connection arrangement, and moves the maximum amount of heat energy. In a series connection arrangement however, each TEM works at half power and moves a lesser amount of heat. Providing a means for the TEMs to change the electrical connections from series to parallel "on the fly" provides a means for control over the heat flux from the device. It is practical to do this both with mechanical relays or using solid-state switches.

In another example, two double pole double throw relays can be used in concert to enable switching circuit connections between two TEMs from a control signal from a microprocessor.

Figure 45:
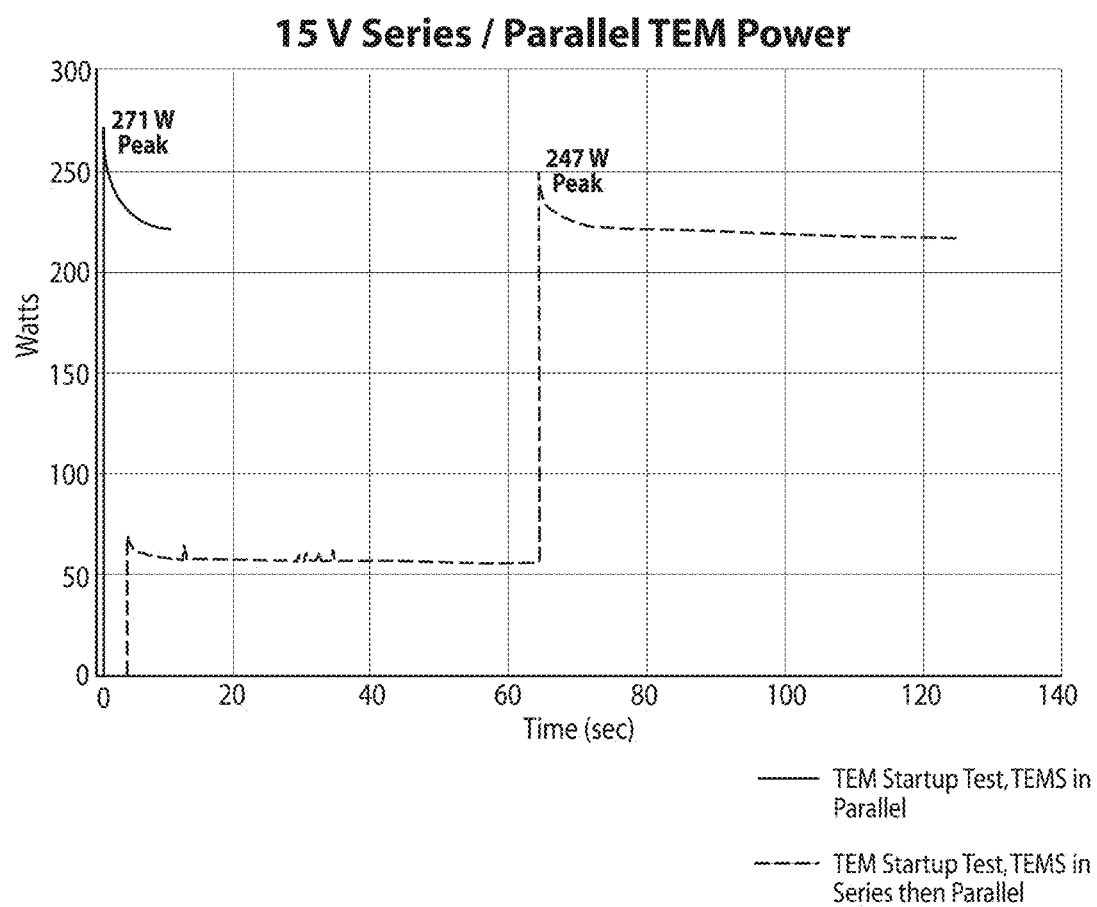
FIG. 45 is a chart showing series and parallel TEM power over time.

FIG. 45 is chart illustrating test data that shows the advantages that a series/parallel circuit can provide, both from the standpoint of current supply and RF noise.

The solid line curve shows the startup power required of two TEMs connected to a 15V power supply in parallel. It can be seen that the peak current rises immediately on startup, since there is no temperature differential at that point and the "back EMF" (electromotive force) or "Seebeck Effect" is zero until a temperature delta across TEM is built from TEM operation. After startup, the Seebeck Effect begins to build and increases the effective resistance to the flow of current through the TEM, so the current, goes down.

The broken line curve shows the startup power required of two TEMs connected to the same 15 V power supply, this time starting in series connection, then switched to parallel after 1 minute. Startup current is very low, and after 60 seconds there is enough temperature difference between the two sides of the TEM to decrease the power requirements to allow a switch to parallel, now requiring 10% less power from the power supply. This in effect allows reduction of the power supply size by 10% peak capacity.

The reverse strategy is also true. After running the TEMs in parallel to achieve maximum cooling and upon reaching the target temperature, the switch can again be made to series connection. This drops the cooling power of the TEMs while still keeping them active, so dramatically reduces temperature overage without turning them completely off and inducing thermal shock when turning them back on again. Switching back and forth from series to parallel across the temperature target thus allows for good temperature control without generating excessive RE energy and without causing undue thermal shock on the module.

Shared Fluid Tank for Radiator Loop and Garment Loop

Generally speaking, the heating/cooling fluid system of the present invention comprises a radiator loop 206 and a garment loop 208, each of which is connected to chiller block 100. Essentially, radiator loop 206 controls the temperature of the chiller block 100, which in turn controls the temperature of the garment loop 208.

Both loops 206, 208 share a single fluid tank 202 for keeping both loops full of liquid as required for proper function of the device 12. A shared tank 202 is advantageous over two individual tanks for numerous reasons, one of which is that it takes up less space, another of which is simplicity of design.

Figure 10A:
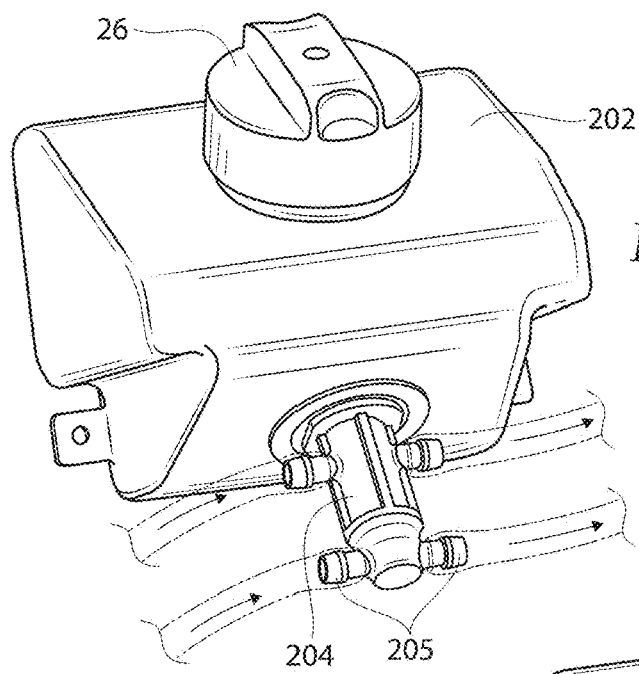
FIGS. 10A-C are perspective views of a fluid tank having alternate port configurations.
Figure 10B:
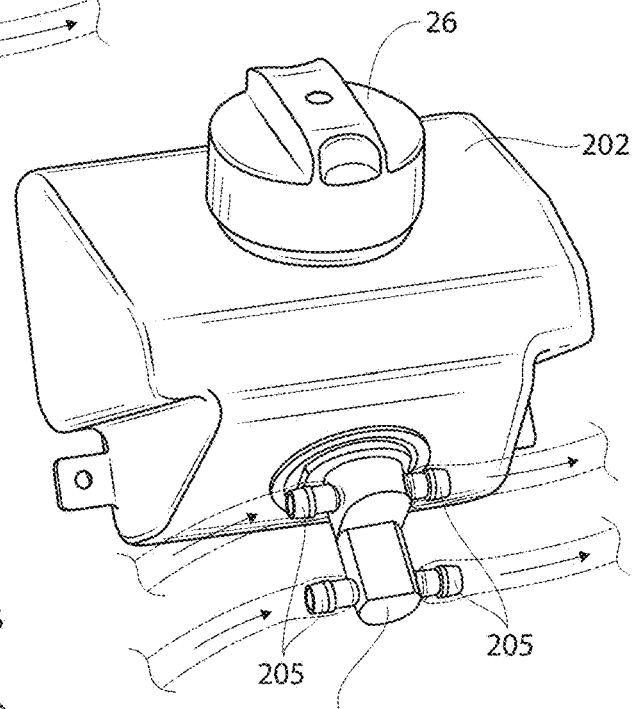
Figure 10C:
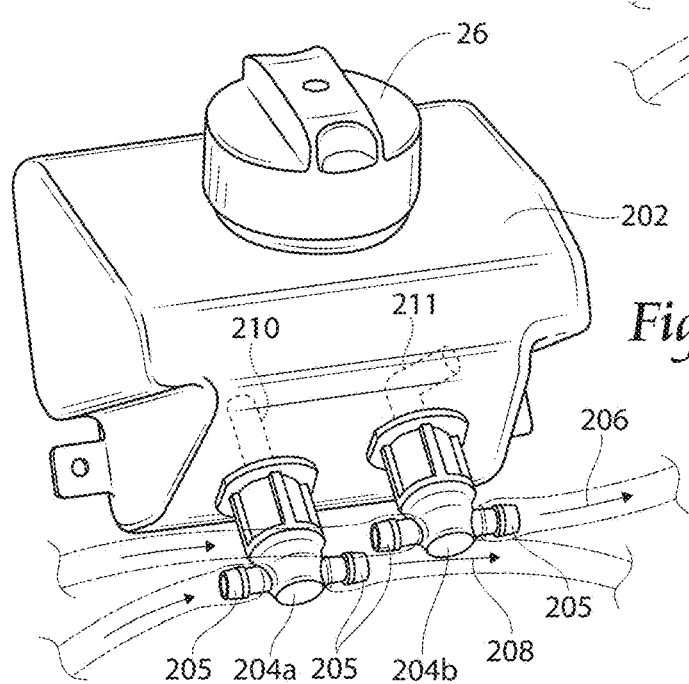
Figure 13A:
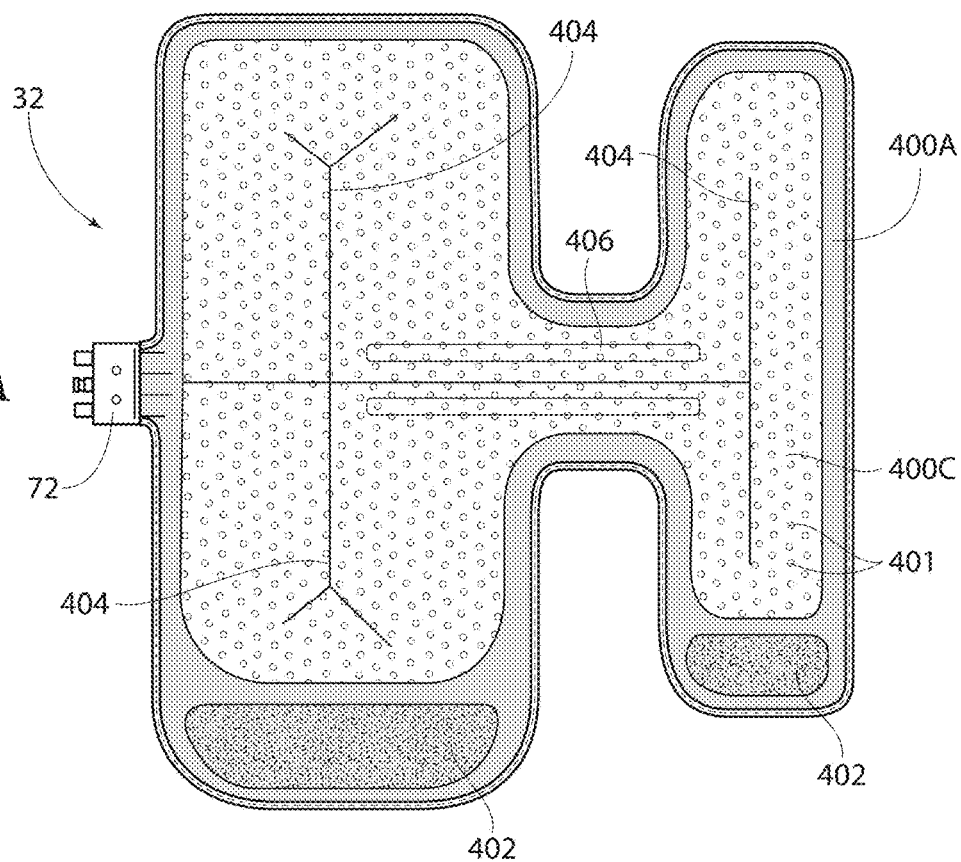
FIG. 13A is a top view of an exemplary thermal garment for wrapping an ankle.
Figure 13B:
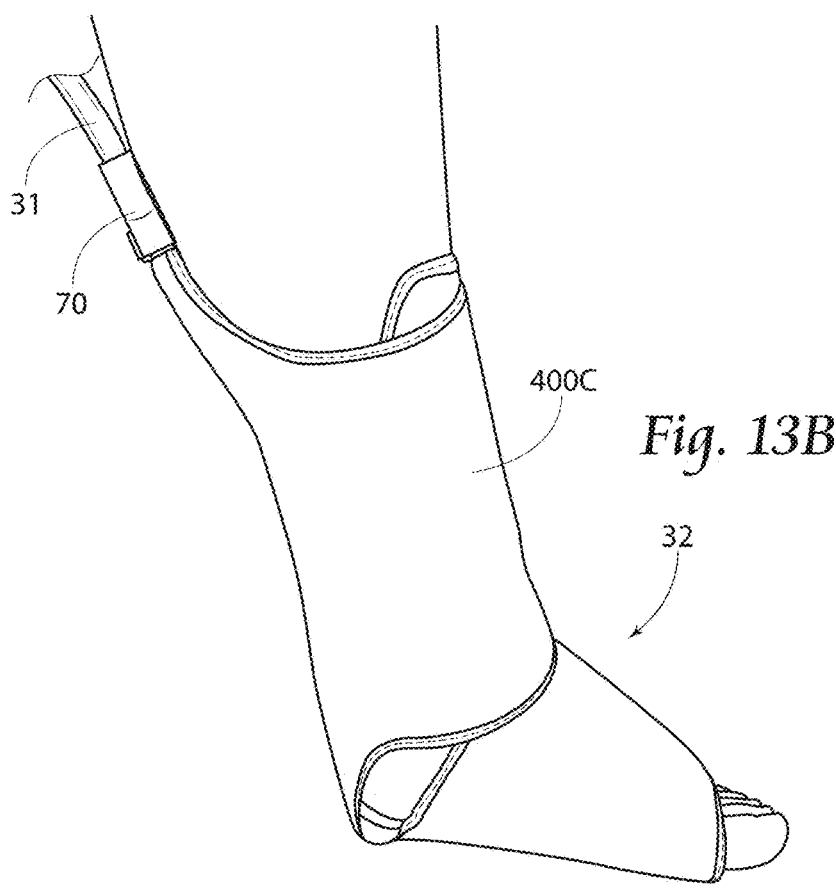
FIG. 13B is a perspective view of the garment of FIG. 13A showing the garment in use.
Figure 14A:
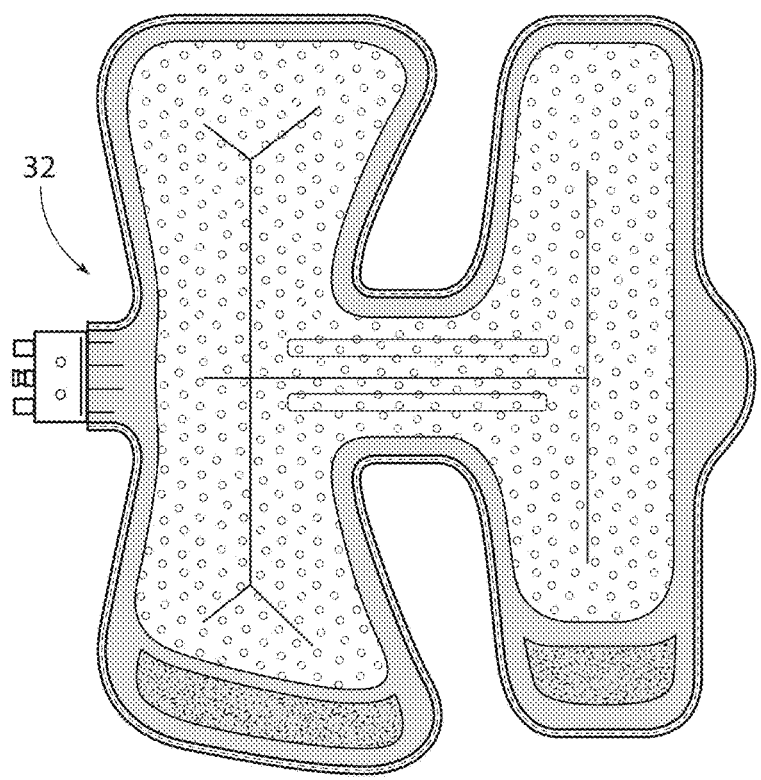
FIG. 14A is a top view of an exemplary thermal garment for wrapping a knee.
Figure 14B:
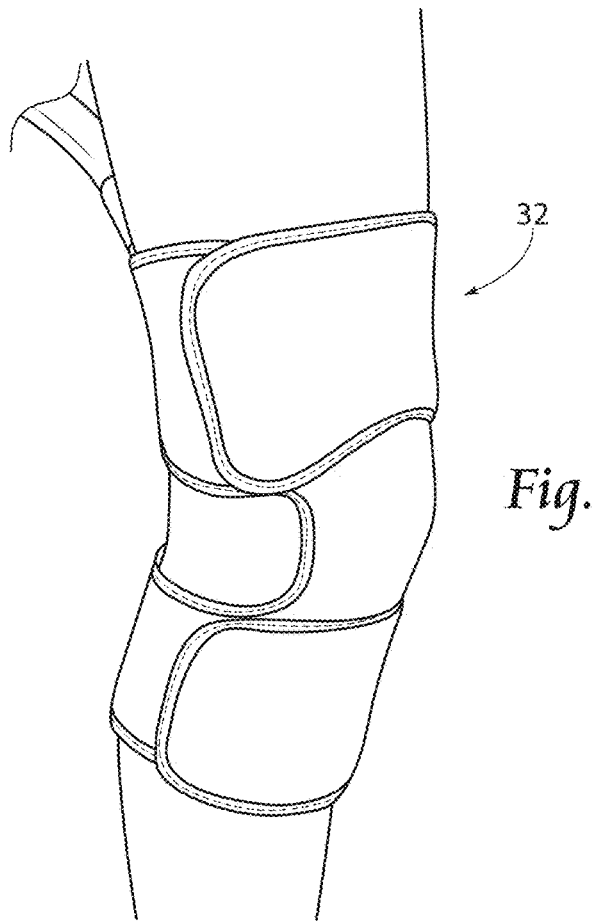
Figure 15A:
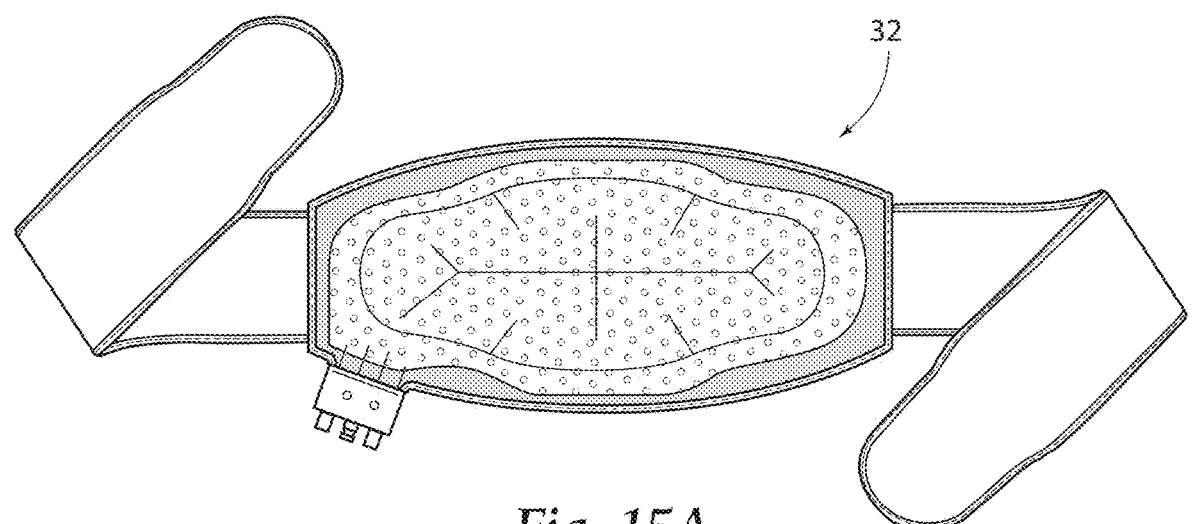
FIG. 15A is a top view of an exemplary thermal garment for wrapping a lower back.
Figure 15B:
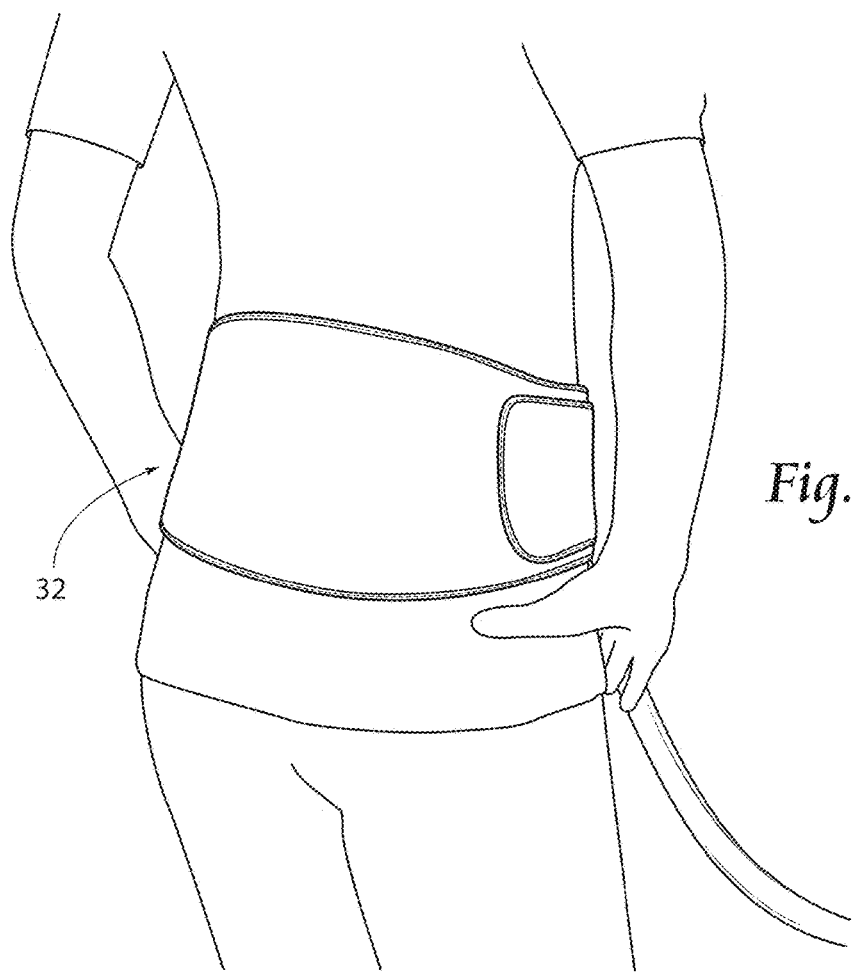
FIG. 15B is a perspective view of the garment of FIG. 15A showing the garment in use.
Figure 16A:
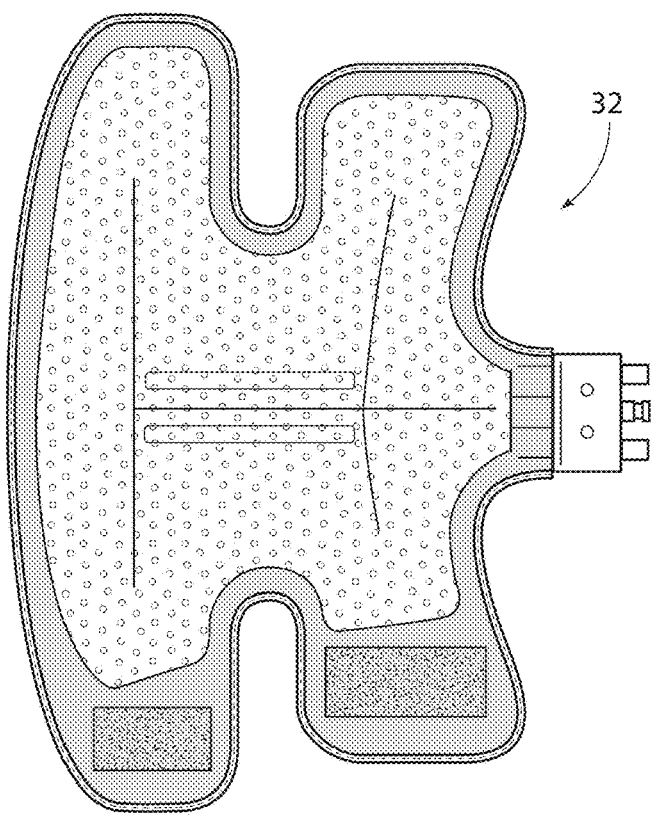
FIG. 16A is a top view of an exemplary thermal garment for wrapping an elbow.
Figure 16B:
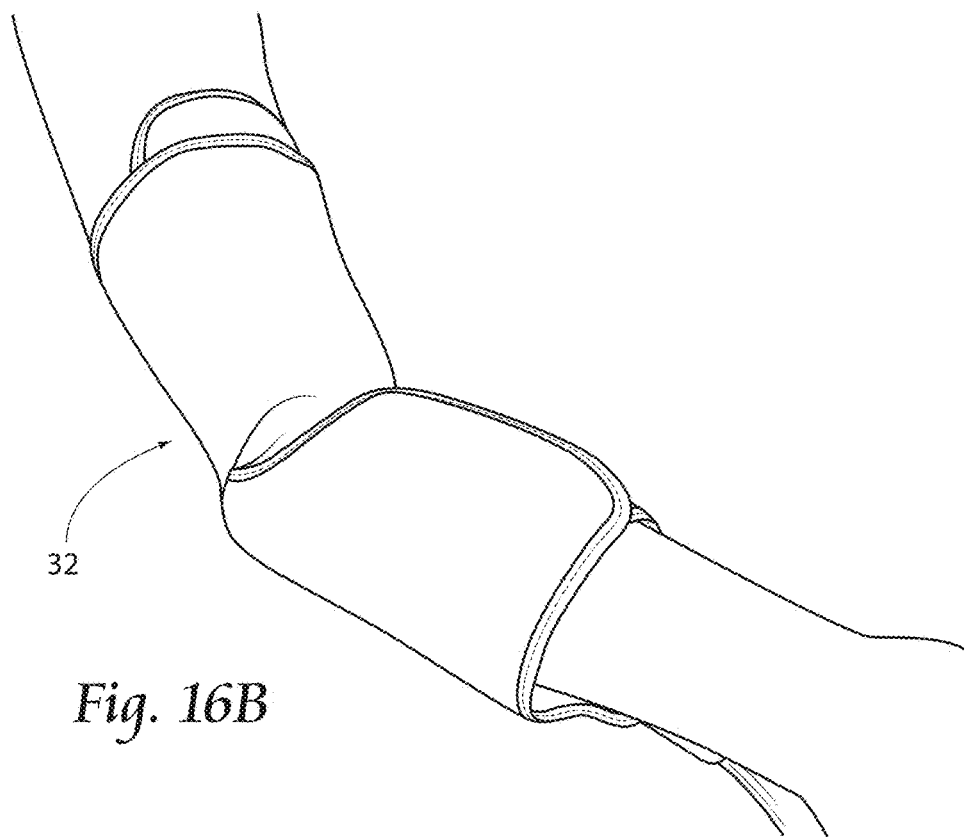
FIG. 16B is a perspective view of the garment of FIG. 16A showing the garment an use.
Figure 17:
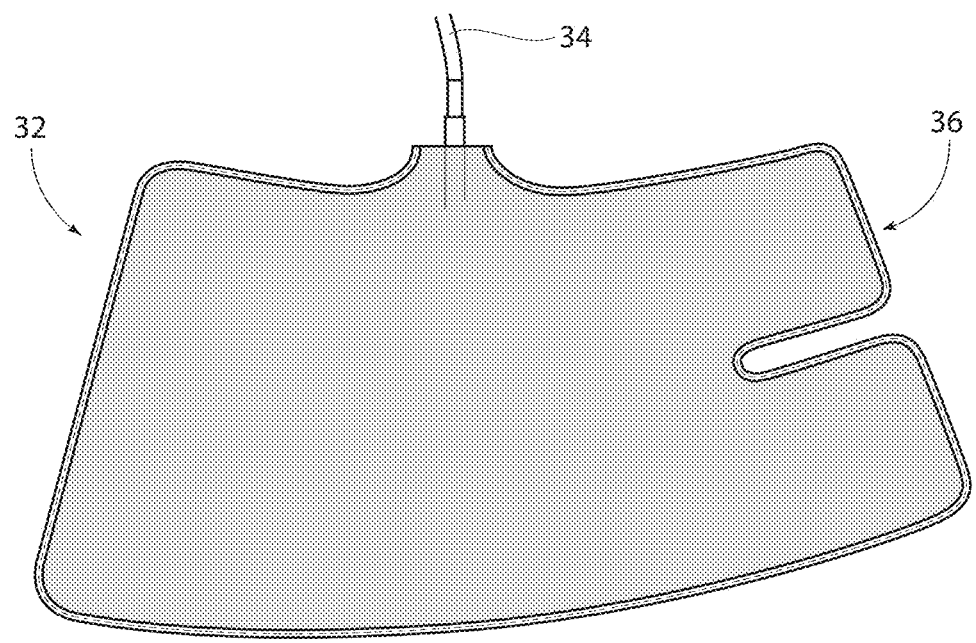
FIG. 17 is a top view of an exterior side of a DVT garment.
Figure 18:
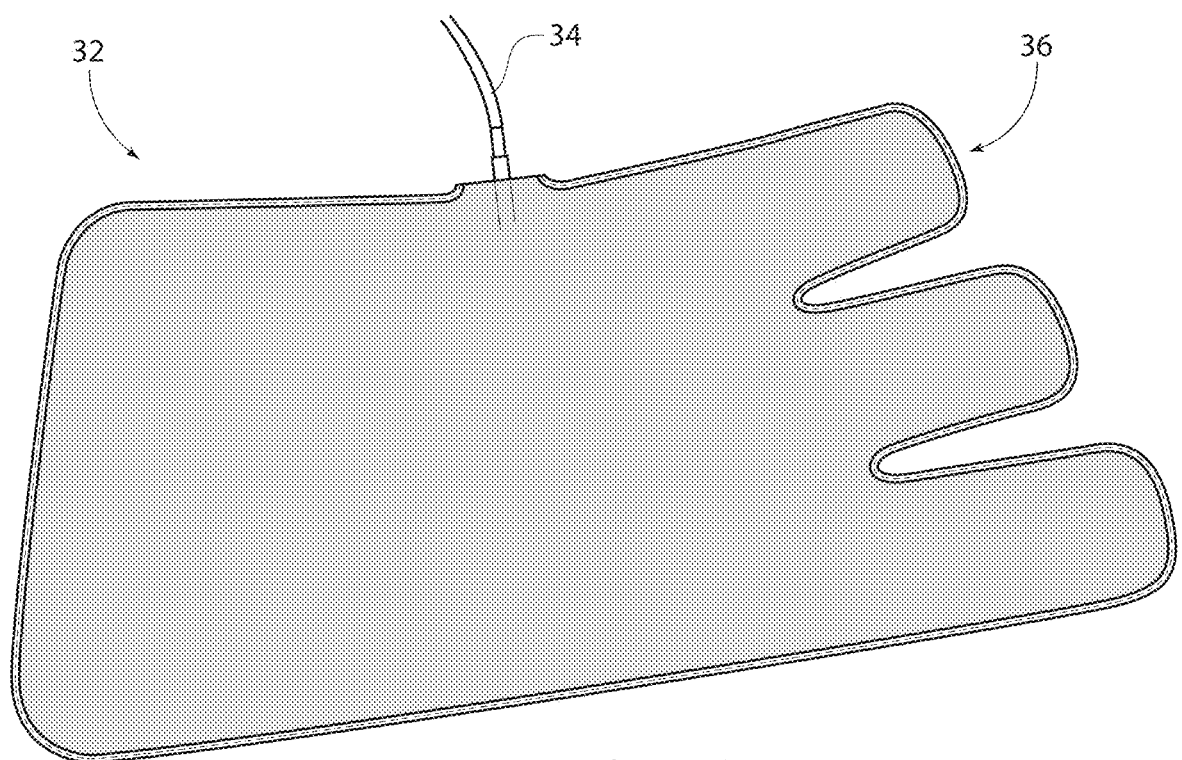
FIG. 18 is a top view of an exterior side of an alternate DVT garment.
Figure 19A:
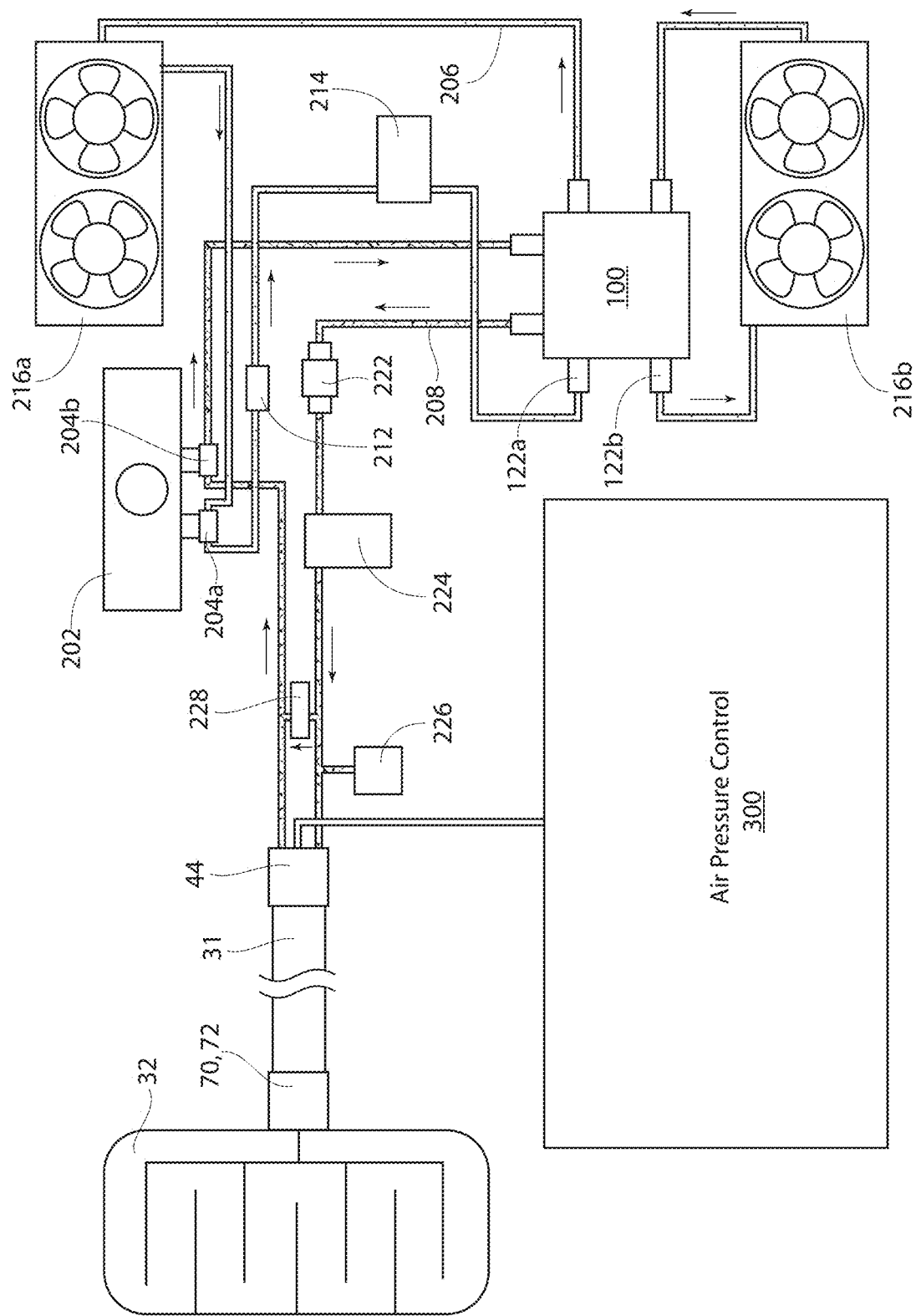
FIG. 19A is a schematic of the air pressure system of one embodiment of the present invention.
Figure 19B:
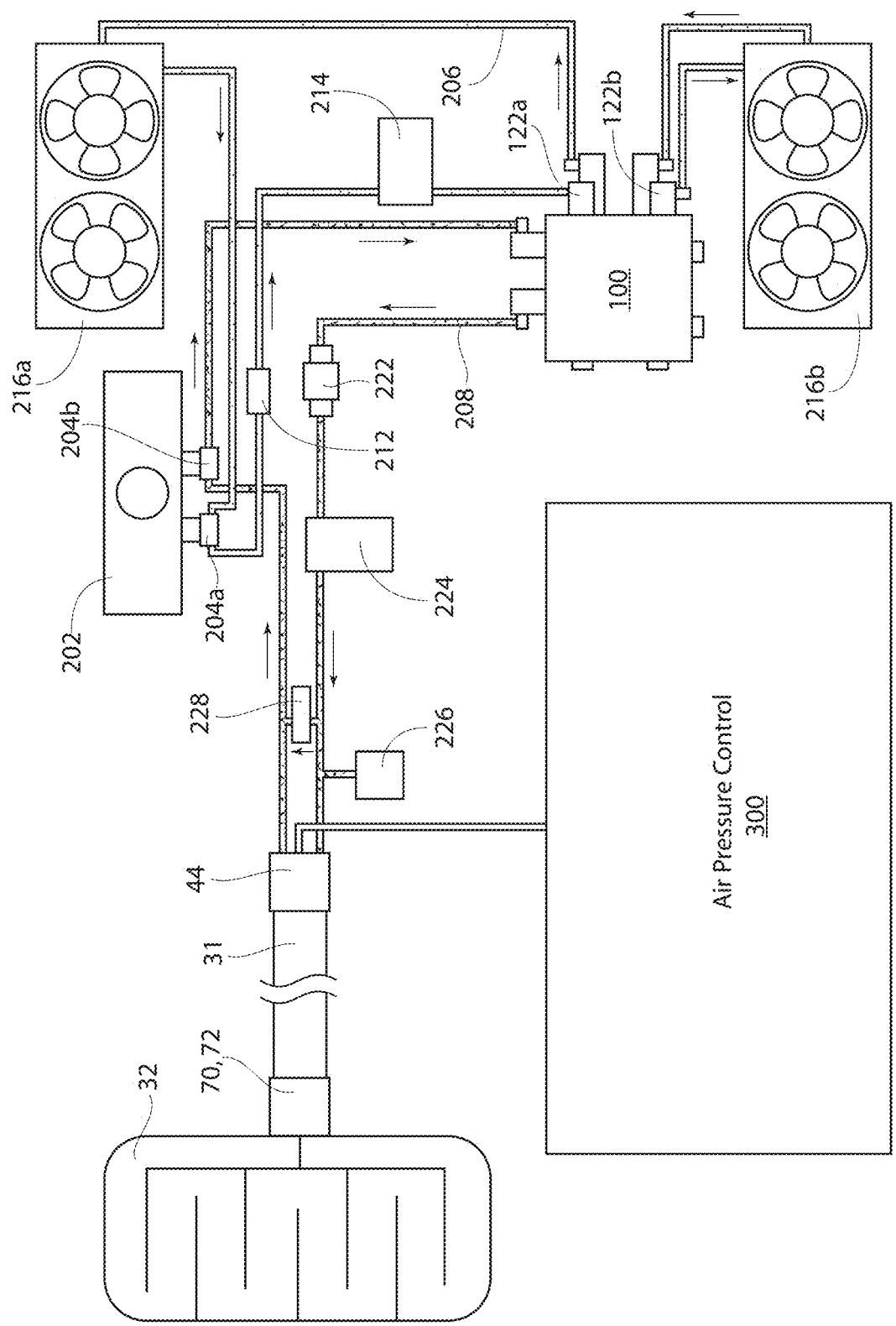
FIG. 19B is a schematic of the air pressure system of another embodiment of the present invention.

Schematic views of embodiments of radiator loop 206 are shown in FIGS. 19A and 19B. Radiator loop 206 can be said to begin with tank 202, which has one or more vapor separators 204 as seen in FIGS. 10A-10C. Referring to FIG. 10C, which shows a currently preferred embodiment, a first vapor separator 204A is provided for radiator loop 206 and second vapor separator 204B for garment loop 208. Each of separators 204 has a nipple 205 or multiple nipples 205 that lead to one of the radiator and garment loops 206, 208.

Radiator loop 206 has a elbow tube 2011 extending into a volume of fluid contained in tank 202, which is in fluid communication with separator 204A. Separator 204A then channels the fluid through a filter 212 or the like if desired, then to a pump 214, then to chiller block 100. Chiller block 100, depending on the thermal settings chosen, either heats or chills the fluid by reversing polarity of the TEMs 104. The fluid then passes through a pair of radiator/fan assemblies 216 in sequence to correct and dissipate fluid temperature, and returns to fluid tank 202.

Note that the arrangement of chiller block 100 and TEMs 104 in radiator loop 206 permits dissipation of excess heat without need for traditional finned heat sinks. The principle advantage to this is that it allows fluid to heat or cool more rapidly and to higher or lower temperatures than traditional TEM arrangements. Another advantage is the reduction in expense and space that the arrangement of the present invention affords over traditional heat sinks.

Referring now to garment loop 208, a straight tube 210 extends from within tank 202 to vapor separator 204B. Elbow tube 211 extends above the surface of the volume of fluid in tank 202 into an air reservoir. Since new garments 32 must be filled with fluid on first use, air residing in the garment must be flushed out to fully fill the garment with fluid. Air is either pushed out of radiator loop 206 and into the reservoir by the bolus of fluid or is entrained in the fluid and released into the reservoir during while fluid passes through the loop 208.

Occasionally tank 202 must be filled by the operator, depending on how often new garments are filled. Radiator loop 206 could theoretically be filled only once when the device is new, and kept filled for the life of the machine by sealing the passages. But practically, over several years a portion of the fluid is lost by way of permeability of the material of the hoses and imperfect seals. This can be minimized by proper hose and other material selections, but cannot be eliminated completely.

However, radiator loop 206 must be kept full of fluid in order to maximize heat transfer. As such, eventually tank 202 must be refilled.

Garment loop 208 can also be said to begin with tank 202, which is in fluid connection with vapor separator 204B. Fluid passes through filter 220 before entering and subsequently exiting chiller block 100. Fluid then passes through a temperature sensor 222, a pump 224, and a pressure sensor 226 before entering garment 32.

Pressure sensor 226 measures average fluid pressure to assess whether there is an overly low pressure such that additional fluid is needed in tank 202. A relief valve 228 is also provided between the ingress of fluid into garment 32 and the egress of fluid away from garment 32. This is so that in the case of overly high fluid pressure, excess fluid is prevented from entering garment 32 and is directed instead back toward tank 202.

Additionally, relief valve 228 opens when device 12 is turned on but no garments are attached. This prevents pump 224 from running continually in an attempt to fill a non-existent garment, thus potentially damaging the pump.

FFT Detection of Low Coolant in Tank

One feature of the present invention is testing the system coolant level in the tank and garment loop system using fast Fourier transforms (FFTs). The system, not shown, uses a piston pump, tubing, and a pressure transducer. These could be a Topsflom piston pump, 3/16 10, 5/16 00 Ark-Plas® urethane tubing, and a 15 PSI Honeywell® pressure transducer.

When the piston pump is activated it runs at approximately 10 Hz. This creates a pressure signature that travels through the tubing and can be read by the pressure transducer. As shown in Fig. 19A (a coordinate grid illustrating a sufficient pressure signature), when an FFT is done to transform this time domain signal into a frequency domain signal, a strong signal can be seen between 8-14 Hz.

However, if the fluid in the machine is low, the pump will not run consistently at that frequency. Rather, air pockets will develop and, as seen in Fig. 19B (a coordinate grid illustrating an insufficient pressure signature), there will foe no peak at the FFT in this region. By using this discrepancy between the 2 FFTs in the 8-14 Hz range it is possible to determine whether or not there is a sufficient supply of fluid in the system using only a single transducer.

This method is an improvement over designs in which a single pressure threshold is used to determine whether the fluid level is sufficiently high. These designs are not as reliable as the FFT detection method because of variation is native pressures of different garments. Using an FFT to determine the magnitude of activity at a given frequency eliminates this problem.

Note that this inventive feature is not limited to use with the apparatus of the present invention. Rather it is applicable anywhere a piston pump or other rhythmic device is acting on a fluid that has potential to be reduced in quantity. Not only is it very reliable in determining fluid level in a closed system, it requires the use of only a single pressure transducer and the capability to perform FFTs.

Air Pressure Control System

Air pressure control system 300 comprises a system of solenoids and air chambers to create, control, and vent air pressure in device 12. Control system 300 provides at least three different pressurized chambers—a chamber 302 for a thermal garment 32, a chamber 304 for a first DVT garment 36a, and a chamber 306 for a second DVT garment 36b. Each of chambers 302, 304, 306 sustains pressures of up to 130 mm Hg and is pressurized using pump 302 of system 300.

Figure 20:
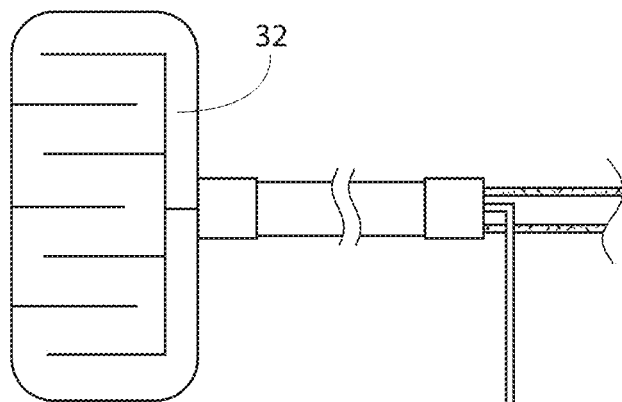
FIG. 20 is a schematic view of an embodiment of an air pressure control system of the present invention.
Figure 20:
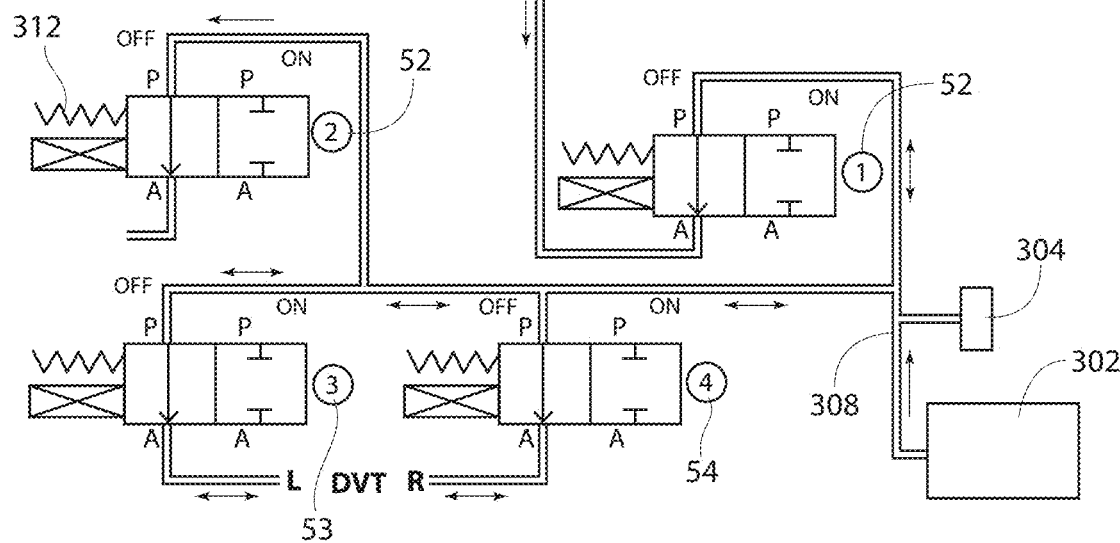
Figure 21:
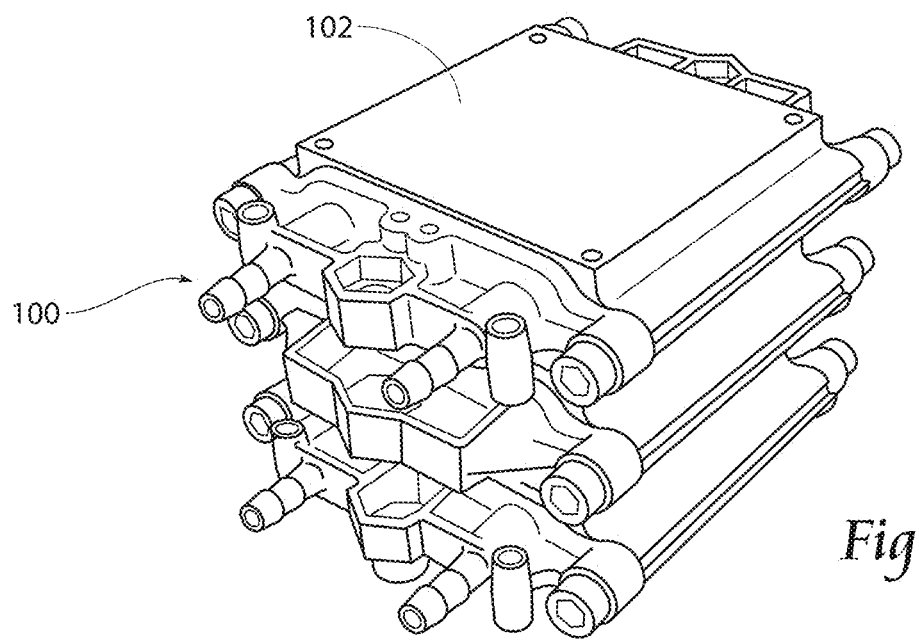
FIG. 21 is a perspective view of an embodiment of a chiller block of the present invention.
Figures 22A, 22B:
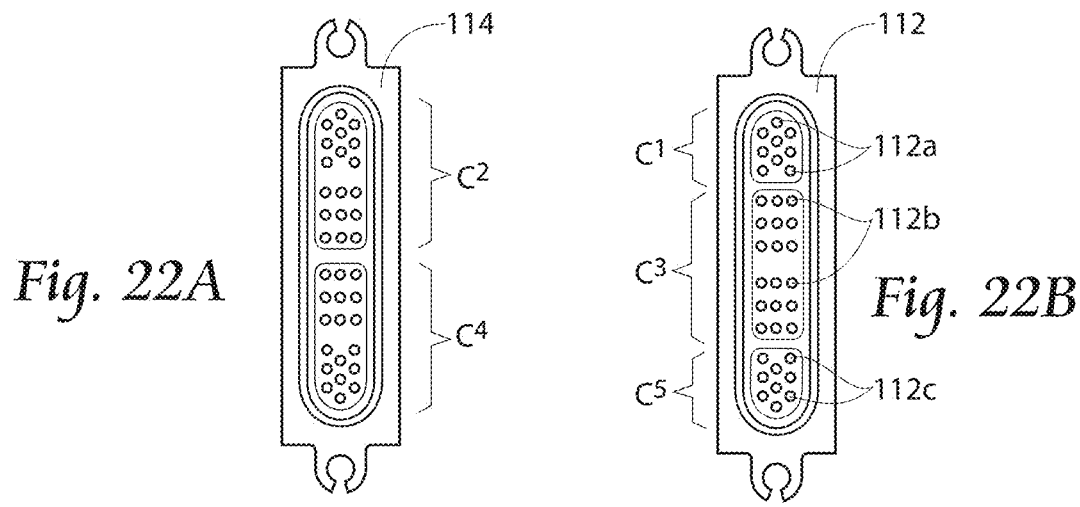
FIGS. 22A and 22B are front views of the chiller block endcaps.

Referring to FIG. 20, a schematic of air pressure control system 300 shows an air supply pump 302, an initial air pathway 308, an air pressure sensor 304, and four solenoid operated switch assemblies S1, S2, S3, and S4, each of which is normally open as shown.

Switch assembly S1 controls the air pressure level in a thermal garment 32. When the thermal garment 32 is not in use, a first solenoid of 310a switch S1 remains closed, preventing air from entering the garment. When the thermal garment is in use, a second solenoid 310b of switch S1 will open and first solenoid 310a will close as pump 302 turns on. This allows air pressure to begin building up within thermal garment 32.

A similar solenoid assembly is present in each of switch assemblies S2, S3, and S4. Switch assembly S2 controls air pressure in system 300 at large by permitting the release of excess air from the system entirely. Each of switch assemblies S3 and S4 are directed to individual DVT units.

The pressure in the DVT chambers is intended to alternate such that when one pressure is at the cycle maximum, the other is near zero. Thus, when the first chamber is being pressurized, solenoids 1, 2, and 4 will be closed and 3 will be open. When the second chamber is being pressurized, solenoids 1, 2, and 3 will be closed and 4 will be open. Once these chambers have reached the requisite pressure, their respective solenoids will be closed until the software calls for then to be vented. At venting, the solenoid attached to the chamber to be vented, as well as solenoid 1, will be opened.

All chambers are preferably pressurized by the single air pump within the system, which has a direct line to all chambers. The single sensor will measure all pressures within the system, using the solenoids to seal off the chambers when the correct pressure has been reached.

Pulsed DVT Cycles

Many DVT prophylaxis cycles have variance in the level of compression they provide to the foot or calf over the duration of their cycles. This is primarily due to the fact that a DVT cycle alternates from fully compressed to empty to encourage blood flow to and from the region to which the DVT garment is applied.

All DVT cycles essentially have an "on" state in which the garment is compressed, and an "off" state in which it does not hold pressure. In the present invention, during the "on" period the pressure provided by the DVT garment will alternate between its maximum pressure and approximately 70% of its maximum pressure every 4 seconds as shown in rig. 43.

User testing has concluded that users prefer this type of pulsed cycle over a more traditional cycle that does not pulse in the "on" position. Increased patient comfort during treatment yields elevated DVT prophylaxis efficacy through increased patient compliance. Not surprisingly, this is more likely to lead to better long-term clinical outcome[1].

[1] Morris, R. J., & Woodcock, J. P. (2004). Evidence-Based Compression. *Annals of Surgery*, 239(2), 162-171.

Figure 44:
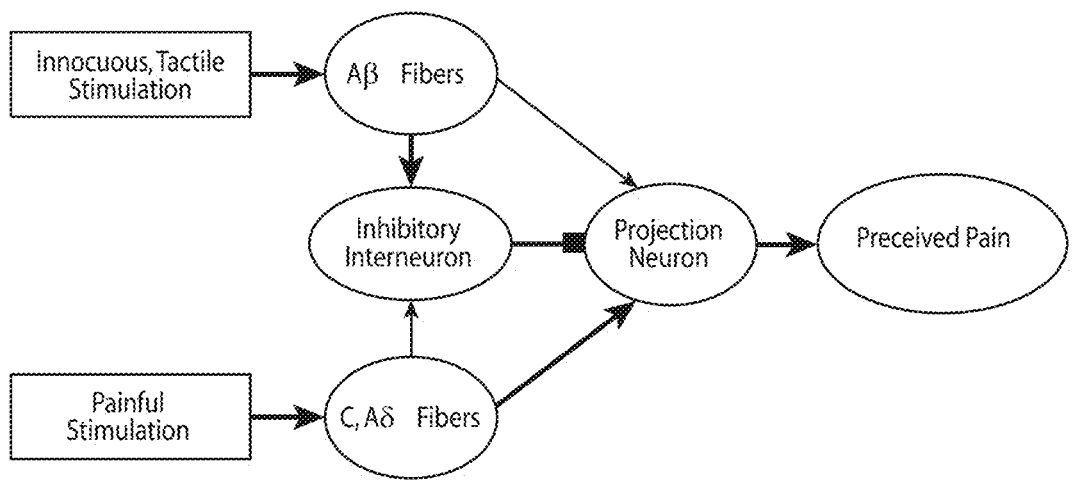
FIG. 44 is a flow chart representation of the pain signal pathway posited by gate control theory.

Additionally, user feedback has indicated that the pulsed DVT prophylaxis leads to temporary relief of chronic localized pain. This is possibly related to a phenomenon known as "gate control theory" which posits that that painful stimuli can be mitigated by the activation of Af3 fibers. Af3 fiber activation promotes inhibitory interneurons, which in turn inhibit the propagation of the pain signals[2]. This process is illustrated in FIG. 44. When Af3 fibers are activated by "innocuous, tactile sensation", such as is provided by a pulsing DVT treatment, the perception of pain may be mitigated[3].

[2] Melzack, R., & Wall, P. D. (1965). Pain Mechanisms: A New Theory. *Science*, 150(3699), 971-978.
[3] Matsumoto, M., Xie, W., Ma, L., & Ueda, H. (2008). Pharmacological switch in Aβ-fiber stimulation-induced spinal transmission in mice with partial sciatic nerve injury. *Molecular Pain*, 4(1), 25.

DVT Gas Pulse Sequence

System 10, and more particularly air pressure control system 300, is controlled by software code to initiate a first pulse of air on initiation of inflation. In a preferred embodiment, the code directs a first pulse of air to ail three garments (thermal garments 32 and DVT garments 36) to jump-start the filling process.

Air pressure control system 300 allows operation of device 12 as a thermal garment only, a thermal garment with a first DVT garment, or a thermal garment with first and a second DVT garments.

In use as a thermal garment only, the dedicated thermal garment is used the same as in connection with other functions. That is, the thermal garment is inflated to apply and maintain heat more effectively to the selected body part, for example, a user's lower back.

When in use with a single DVT garment, the dedicated DVT garment is inflated to apply pressure to a different body part, for example a user's right leg, and after inflation performs a therapeutic pulsing cycle.

If a second DVT garment is in use, the first DVT garment is deflated and the second DVT garment is inflated to apply pressure to yet another body part, for example a user's left leg. A therapeutic pulsing cycle is then performed with the second DVT garment.

Figure 42:
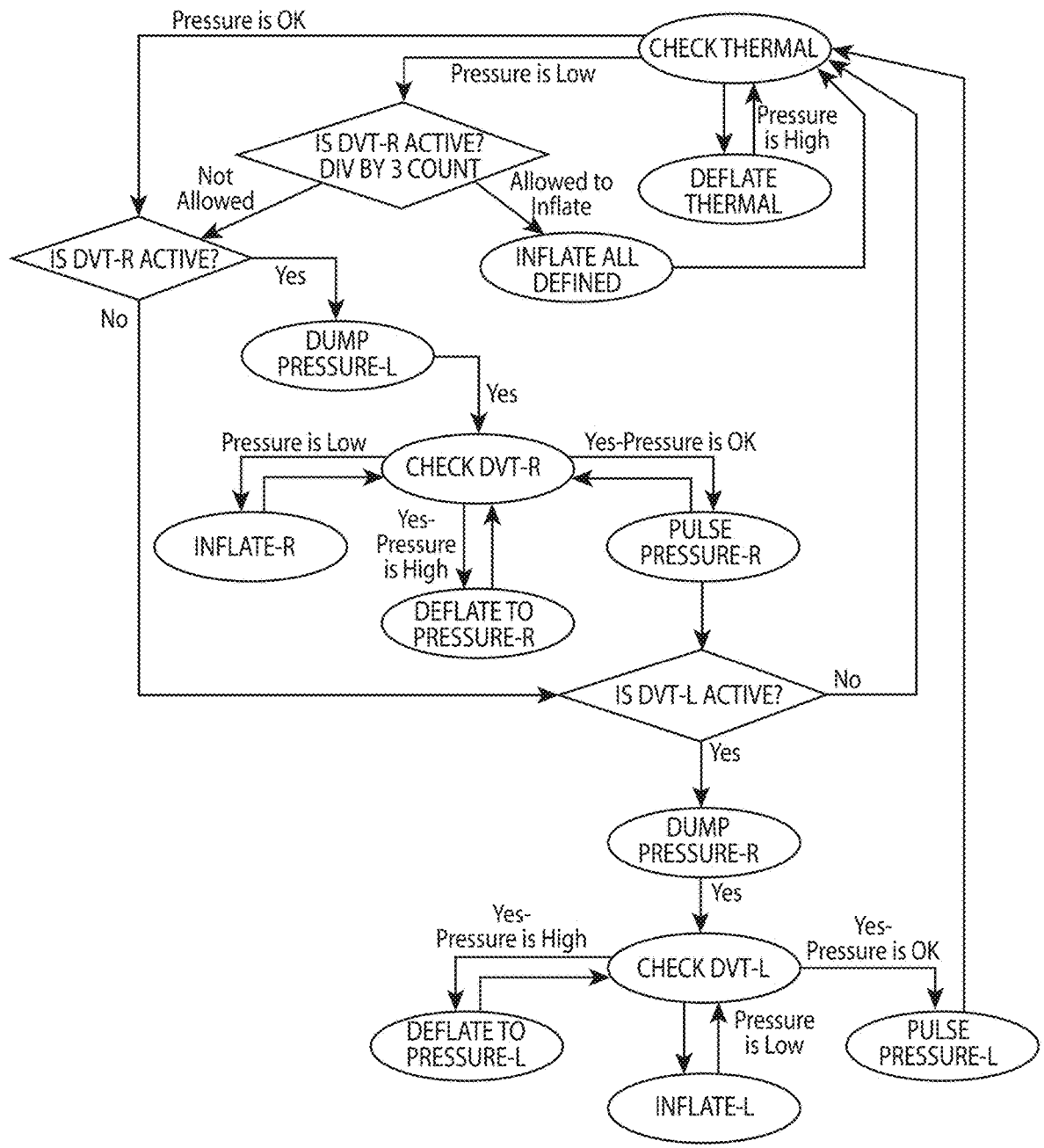
FIG. 42 is a flow chart representation of a therapeutic pulsing cycle.
Figure 43:
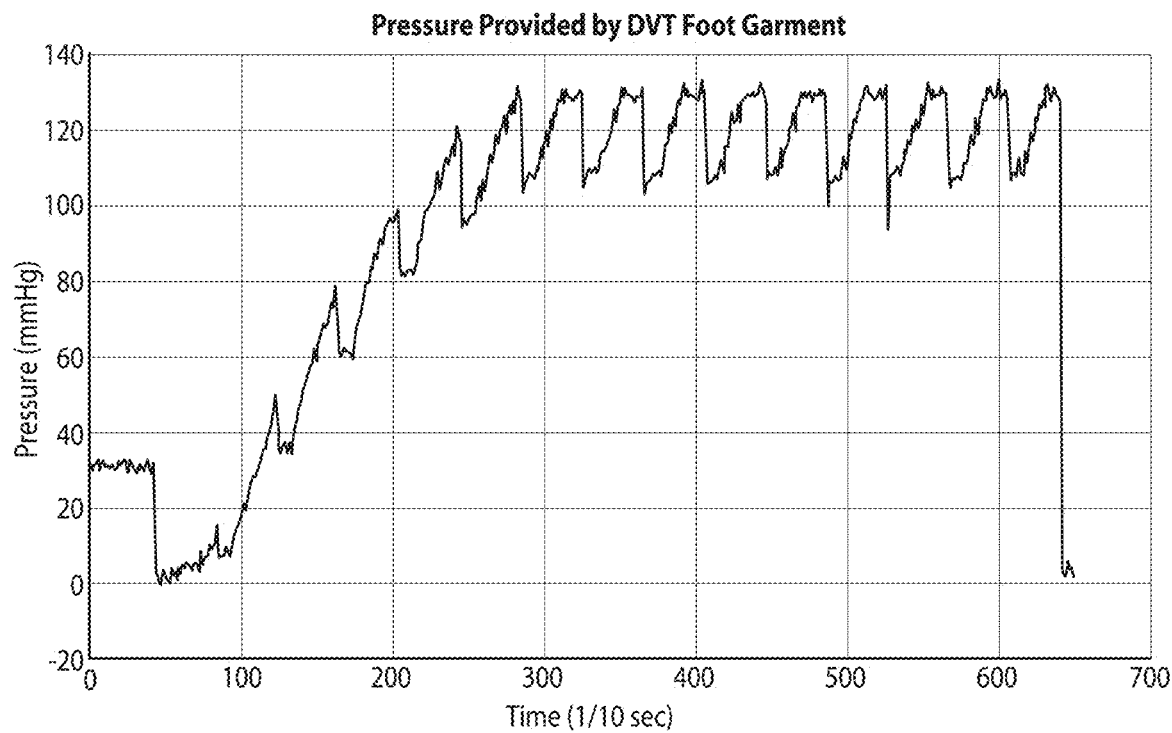
FIG. 43 is a chart showing pulsed DVT cycle pressure over time.

A representation of this cycle profile is shown in FIG. 42. As can be seen, in the event the device is being used only as a thermal garment, the cycle begins with "check thermal". Pressure at the thermal garment will, at this point, be low, so the decision step "is DVT-1 active? divide by 3 count" is engaged. Since DVT-1 in this scenario is net active, the step of inflation of all connected garments is performed and the thermal garment pressure is again examined.

Once the thermal garment pressure reaches its defined pressure point, a second decision point is engaged, i.e. "is DVT-1 active?" Again, the first DVT garment in this scenario is inactive, so a third decision point, "is DVT-2 active?" is reached, and, the answer being no, the system returns to "check thermal."

When a first DVT garment is employed with the thermal garment, at the "is DVT-1 active? divide by 3 count" decision point, the DVT-1 garment is active and the "divide by 3 count" step is engaged. Because this is the beginning of the first cycle, there have been zero full cycles, and zero divided by three is zero. Whenever the answer to the question is anything other than zero, inflation is not allowed. However, because the answer in this case is zero, all attached devices are allowed to be inflated as needed.

Again, once the thermal garment pressure reaches its defined pressure point, the decision "is DVT-1 active?" is reached, but now the first DVT garment is active, so ail pressure to DVT-2 is dumped. In this scenario, there is no pressure at DVT-2 because it is not being employed. DVT-1 is uninflated, so pressure will be low such that DVT-1 is inflated until the appropriate pressure is reached. The therapeutic pulse cycle is ensues after which, since DVT-2 is not active, the system returns to the check thermal step.

This time at the "is DVT-1 active? divide by 3 count" decision point, since one cycle has been completed, the "divide by 3 count" answer is one divided by three, i.e. not zero. As such, inflation of all attached device is not allowed and the cycle continues from there.

Only after the 3rd cycle will the answer to "divide by 3 count" be zero again, at which point all attached devices will be allowed to inflate again.

Naturally, each of the thermal garment and first and second DVT garments can be used in the same therapy session as well. This iteration differs only slightly from the thermal garment+single DVT garment scenario, except that at "is DVT-2 active?" the answer is yes and the DVT-2 garment cycle is performed. This includes dumping pressure at the DVT-1, inflating and/or deflating the DVT-2 pressure as needed, and performing an additional therapeutic pulse step.

Programmed Cycle Software

Many medical professionals recommend different treatments for injuries during different periods of injury recovery. For instance, immediately after an injury occurs most professionals will recommend cooling and compressing the injured area to prevent secondary injury and mitigate swelling. However, after a period of time has passed, most will recommend a change of treatment to a warm thermotherapy cycle for its analgesic effect and encouragement of blood flow to an area.

Advantageously, the cryotherapy device of the present invention is capable of having multiple cycle programs that run automatically based on a clock internal to the device. This permits the pre-programming of prescribed cycles, typically by a medical professional, so that even in outpatient care the preferred treatment regimen can be followed automatically.

Password Protection

To ensure proper use of the device for the best thermal outcome, as well as to prevent misuse of the device, a password may be required in order to modify the pre-programmed therapy instructions.

Therapy Tracking

Methods of tracking patient compliance are contemplated so that care providers know not only what regimen of therapy was prescribed but also what therapy was actually performed throughout the patient's therapy history. This information can useful for the provider who may be receiving mistaken or only partial information about therapy performance.

To this end, a USB port can be provided for relaying system information, including therapy history, to an external device such as a computer. The history can be added to a patient's file for future reference. For the researcher, such a record of therapy, when aggregated with numerous other patient histories, presents a useful dataset. Such information could direct improvements for future treatment protocol.

As previously noted however, in the present embodiment USB port 22 is a convenience enabling a user to charge a phone or the like while device 12 is powered.

Garment Materials

Referring to thermal garment 32 as described herein passim, an internal fabric layer 400*a* and an external fabric layer 400*b* are presented as well as a thermal contact layer 400*c*. Fabric layers 400*a*, 400*b* may be constructed of any suitable material.

Contact layer 400*c* comprises a bladder, preferably constructed of a puncture resistant but flexible material. The patient contact side of contact layer 400*c* may further be provided with a plurality of protrusions 402 that provide even closer contact between layer 400*c* and the patient body part.

A DVT garment 36, which fills with compressed air but not fluid, does not require internal fluid structures, only an internal air bladder 410 connected to an air supply. Garment 36 has inner and outer fabric layers 412*a*, 412*b*.

Garment Configuration

As shown in FIGS. 12-16, a number of garment configurations are possible to provide heat therapy proximate to the body part requiring treatment. These include but are not limited to the configurations shown for use with a patient's foot, ankle, knee, lower back, and elbow.

FIGS. 17 and 18, 35, and 37 illustrate DVT-only garments, again designed to provide therapy to the targeted body part.

FIGS. 36 and 38-41 show additional embodiments of a thermal garment of the present invention, including features such as elbow/knee openings 414, body straps 416, sling straps 418, and adjustment/closure patches 420.

Thermal Garment Construction

When the circulating liquid through a thermal garment 32 for application to a patient's joints, such as elbows and ankles, garment 32 itself must be able to conform to the joints. Fold lines 404 are provided to ease wrapping of garment 32 around a joint.

In addition, bending the liquid conduit around a body part can crimp the conduit. This stops the flow of the liquid that would normally circulate through the entire garment, creates back pressure in the garment, and, naturally, limits the effectiveness of garment. One design uses hollow tubing embedded in the areas where the garment has a tendency to become kinked. The tubing provides a rigid structure that prevents a patient's arm, for instance, from pinching off the liquid to the bladder even when the patient bends the arm. Proper flow ensures that the patient receives uncompromised treatment.

Also, when cooled or heated fluid is circulated within garment 32 at a desired therapeutic temperature, the fluid temperature is normalized by the atmospheric temperature, raising or lowering the fluid temperature accordingly. The effectiveness of the therapeutic regimen can therefore be negatively impacted by the external temperature.

To avoid temperature degradation of the fluid, the present invention may include an insulated layer system within the design of garment 32. Specifically, a three-fabric layer system is envisioned in which insulating layers 404*a*, 404*b* are provided over the front and rear sides of contact layer 400*c*. The fluid is therefore provided with more insulation against the effects of ambient air, leading to more effective treatment.

Slip-on Foot DVT Embodiments

For patients with diabetes, lymphedema, high blood pressure, or other conditions that cause edema (foot swelling due to fluid buildup), DVT compression of the feet is of particular importance.

Whether the edema is caused by standing for long hours, such as is required in a number of professions, or simply from sitting at a desk all day, DVT compression of the feet is beneficial.

To provide such patients with an option that would allow DVT compression cycles while standing or sitting, but also allow for quick removal of a DVT garment when walking is required, slip-on foot garments are envisioned. See FIGS. 48*a*, 48*b*, 48*c*. For example, a desk worker could remove his or her shoes once seated and insert them into a DVT foot garment located under his or her desk. When the patient needs to get up, he or she simply removes his or her feet from the slip-on DVT garment and back into his or her shoes.

A person standing behind a counter, such as a cashier, could likewise remove shoes and slip feet into a DVT foot garment, replacing his or her shoes when not behind the counter. Even a person who is usually in motion could readily and rapidly employ such a garment during scheduled breaks.

A number of embodiments are envisioned. For example, a DVT insert might be provided for a pair of store-bought slippers, or a slipper having integral DVT chambers could be made. A single unit having a single DVT foot chamber or two individual chambers are also envisioned. Other embodiments that could provide slip-on convenience or foot DVT are likewise considered, as are other slip-on or other easy-on, easy-off configurations for other parts of the body. In addition, the foot DVT could be manufactured complete or made to be adapted to commercially available foot accessories.

Patient Name Tag

Safety concerns regarding sanitation, as codified in FDA regulations, prevent multiple users from using the same garment. One way to address this is to pr vide reusable garment covers to each patient with a single insert. However, a garment cover invariably reduces the ability of the insert to heat or cool the intended body part. Further, the garment covers themselves are, at least at present, almost as expensive as the garment itself.

Since it is envisioned that each patient will be provided with his or her own garment(s), especially where treatment will be provided in a group setting, such as a clinic or sports facility, it is advantageous to provide the garments with identity indicia. Such indicia could range from name tags to patient, numbers, so long as they provide the ability for patients and/or providers to identify an individual's personal garment(s).

We claim:

1. A therapeutic thermal compression device comprising:
   a temperature system, a compression system, and a control system, wherein said temperature system comprises a heating cooling assembly having an upper, a center, and a lower plate, and a first and a second thermoelectric module (TEM), said first TEM being interposed between said upper and center plates and said second TEM being interposed between said center plate and said lower plate,
   a radiator portion separate from said temperature system and from said heating/cording assembly, said radiator portion and said temperature system connected to a fluid tank;
   a fluid pump portion connected with said fluid tank;
   a liquid being circulated through said radiator portion and said temperature system without passing through said fluid tank;
   wherein said liquid is heated or cooled by said TEMs by passing said liquid through said heating/cooling assembly of said temperature system.

2. The device of claim 1, wherein said upper, center, and lower plates are substantially identical to one another and are stacked such that each of said upper and lower plates are disposed along a first axis and said center plate is disposed along a second axis oriented 180 degrees from said first axis.

3. The device of claim 1, wherein each plate is provided with a plurality of bores for said liquid to pass through, and a pair of plate endcaps are associated with each plate for retaining said liquid within said bores, said endcaps bearing at least one inlet or outlet structure and a related conduit.

4. The device of claim 3, wherein said bores and said endcaps are configured such that said liquid passes through a length of each said plate at least once in a first direction and at least once in a second direction.

5. The device of claim 1, wherein heating is achieved by changing said first and said second TEMs to a first polarity and cooling is achieved by reversing a current of said TEMs to a second polarity.

6. The device of claim 1, wherein the fluid connection between each of said radiator portion and fluid pump portion include a vapor separator.

7. The device of claim 1, wherein fluid that has been heated or cooled by said heating/cooling assembly is further adiusted by said control system to a desired temperature.

8. The device of claim 1, further comprising a patient garment to be filled with a desired amount of fluid by way of said fluid pump portion and at a desired e a temperature by way of said temperature control system.

9. The compression system of claim 1, further comprising an air supply assembly having a pump, a pressure sensor, and at least one air chamber connected to at least one switch for providing air to a patient garment.

10. The compression system of claim 9, comprising at least three air chambers, each of which is opened or closed by way of an associated one of said switches.

11. The compression system of claim 10, wherein at least one of said air chambers is connected with at least one patient garment.

12. The compression system of claim 11, wherein a first chamber of said air chambers is connected with a first garment, a second chamber of said air chambers is connected with a second and a third chamber of said air chambers is connected with a third garment.

13. The control system of claim 1, further comprising an input arrangement for controlling said temperature system and said compression system.

14. The input arrangement of claim 13, further comprising a touch-screen interface.

15. A method of providing a patient with therapeutic thermal compression comprising the steps of:
    selecting a thermal compression garment;
    connecting said thermal compression garment to a fluid temperature system incorporating a heating/cooling assembly having an upper, a center, and a lower plate and a first thermoelectric module (TEM) and a second thermoelectric module (TEM), said first TEM being interposed between said upper and center plates and said second TEM being interposed between said center plate and said lower plate, said fluid temperature system further comprising a circulating liquid providing the necessary heating and cooling for said fluid temperature system independent of a radiator,
    connecting said garment to an air compression system, providing fluid or air to said garment, and
    controlling the temperature of said fluid to said garment;
    controlling the air pressure to said garment;
    delivering a first temperature to the garment for a first temperature duration and a second temperature for a second temperature duration; and
    delivering a first pressure to the garment for a first pressure duration and a second pressure for a second pressure duration.

16. The method of claim 15, whereby said first temperature, said first temperature duration, said second temperature, said second temperature duration, said first pressure, said first pressure duration, said second pressure, and said second pressure duration are each individually selectable.

17. The method of claim 15, wherein the step of selecting said at least one thermal compression garment based on the body part intended for treatment.

18. The method of claim 15, further delivering third pressure to the garment for a third pressure duration.

* * * * *

UNITED STATES PATENT AND TRADEMARK OFFICE
CERTIFICATE OF CORRECTION

PATENT NO. : 11,638,675 B2
APPLICATION NO. : 16/183398
DATED : May 2, 2023
INVENTOR(S) : Binversie et al.

Page 1 of 1

It is certified that error appears in the above-identified patent and that said Letters Patent is hereby corrected as shown below:

In the Claims

Claim 1, Column 15, Line 33: "heating cooling" should read --- heating/cooling ---

Claim 1, Column 15, Line 40: "heating/cording" should read --- heating/cooling ---

Signed and Sealed this
Twenty-seventh Day of May, 2025

Coke Morgan Stewart
*Acting Director of the United States Patent and Trademark Office*